United States Patent [19]
Noriega et al.

[11] Patent Number: 5,783,196
[45] Date of Patent: Jul. 21, 1998

[54] GUA MUTANTS OF SHIGELLA SPP. AND VACCINES CONTAINING THE SAME

[75] Inventors: Fernando R. Noriega, Baltimore; Myron M. Levine, Columbia, both of Md.

[73] Assignee: University of Maryland at Baltimore, Baltimore, Md.

[21] Appl. No.: 629,600

[22] Filed: Apr. 9, 1996

[51] Int. Cl.$^6$ .................................................. A61K 39/02
[52] U.S. Cl. ........................... 424/234.1; 424/235.1; 435/172.3; 435/252.1; 935/55; 935/72
[58] Field of Search ........................ 424/235.1, 234.1

[56] References Cited

U.S. PATENT DOCUMENTS 5,077,044  12/1991  Stocker .................................. 424/235.1

OTHER PUBLICATIONS

McFarland et al, *Microbial Pathogenesis*, 3:129–141 (1987).
Bacon et al, *Br. J. Exp. Path.*, 31:714–724 (1950).
Hoiseth et al, *Nature*, 291:238–239 (1981).
Edwards et al, *J. of Bacteriology*, 170(9):3991–3995 (1988).
Levine et al, *J. Clin. Invest.*, 79:888–902 (1987).
Levine et al, *Reviews of Infectious Diseases*, 11(Supplement 3):S552–S567 (1989).
O'Callaghan et al, *Infection and Immunity*, 56(2):419–423 (1988).
Sigwart et al. *Infection and Immunity*, 57(6):1858–1861 (1989).
Verma et al, *Vaccine*, 9:6–9 (1991).
Kärnell et al, *Vaccine*, 11:830–836 (1993).
Noriega et al, "Construction and Characterization of Oral Attenuated Shigella Vaccine–Candidates and Their Potential Use as Live Vector–Hybrid Vaccines", 29th Joint Conference on Cholera and Related Diarrheal Disease, Abstract, pp. 166–168 (Dec. 3, 1993).
Gilbert et al, Biochem. J, vol. 191(2), pp. 533–542, 1980.
Noriega, FR et al, Am. Soc. of Microbiol, vol. 34, p. 188, 1994.
Lindberg, et al, Dev. Biol. Stand, vol. 84, pp. 211–219, 1995.
Nataro, JP et al, Infect. & Immun., Dec, vol. 63(12), pp. 4721–4728, 1995.
McFarland, William C et al, Microbial Pathogenesis, vol. 3, pp. 129–141, 1987.
Tesfa–Selase et al, Mol. Gen. Genet., vol. 231, pp. 256–264, 1992.
Murray, BE et al, J. of Bacteriology, Aug. pp. 5216–5223, vol. 175(16), 1993.
Neidhardt, FC, *Escherichia coli* and *Salmonella typhimurium*: Cellular and Molecular Microbiol., section 29, Purines & Pyrimidines p. 449, 1987.

*Primary Examiner*—Christopher L. Chin
*Assistant Examiner*—Ginny Allen Portner
*Attorney, Agent, or Firm*—Sughrue, Mion, Zinn, Macpeak & Seas, PLLC

[57] ABSTRACT gua mutants of Shigella spp., and vaccines containing the same are disclosed.

21 Claims, 12 Drawing Sheets

FIG. 2A

```
                                                          AlwI
                                                           |
GTAAAGTACCAGTGACCGGAAGCTGGTTGCGTGAAATTAGAAATTTCGCCGCTGATCCAA    60
CATTTCATGGTCACTGGCCTTCGACCAACGCACTTTAATCTTTAAAGCGGCGACTAGGTT

HinfI
                                  |
ACCTGTCCCATCTCATGCTCAAGCAGCAGACGAACCGTTTGATTCAGGCGACTAACGGTA   120
TGGACAGGGTAGAGTACGAGTTCGTCGTCTGCTTGGCAAACTAAGTCCGCTGATTGCCAT NspHI
              AflIII                                BspMI
                |                                     |
AAAATTGCAGGGGATTGAGAAGGTAACATGTGAGCGAGATCAAATTCTAAATCAGCAGGT   180
TTTTAACGTCCCCTAACTCTTCCATTGTACACTCGCTCTAGTTTAAGATTTAGTCGTCCA TATTCAGTCGATAGTAACCCGCCCTTCGGGGATAGCAAGCATTTTTTGCAAAAAGGGGTA   240
ATAAGTCAGCTATCATTGGGCGGGAAGCCCCTATCGTTCGTAAAAAACGTTTTTCCCCAT SfaNI                    SacII SspI   MseI
  |                        |    |      |
GATGCAATCGGTTACGCTCTGTATAATGCCGCGGCAATATTTATTAACCACTCTGGTCGA   300
CTACGTTAGCCAATGCGAGACATATTACGGCGCCGTTATAAATAATTGGTGAGACCAGCT SnaBI
           |
GATATTGCCCATGCTACGTATCGCTAAAGAAGCTCTGACGTTTGACGACGTTCTCCTCGT   360
CTATAACGGGTACGATGCATAGCGATTTCTTCGAGACTGCAAACTGCTGCAAGAGGAGCA DdeI    PvuII
                                       |       |
TCCTGCTCACTCTACCGTTCTGCCGAATACTGCTGACCTCAGCACCCAGCTGACGAAAAC   420
AGGACGAGTGAGATGGCAAGACGGCTTATGACGACTGGAGTCGTGGGTCGACTGCTTTTG EcoRII
                                                    BstNI
                                           BssHII    |
                                              |      |
TATTCGTCTGAATATCCCTATGCTTTCCGCAGCAATGGATACCGTAACGGAAGCGCGCCT   480
ATAAGCAGACTTATAGGGATACGAAAGGCGTCGTTACCTATGGCATTGCCTTCGCGCGGA NspHI
          DdeI                                  AflIII
            |                                     |
GGCTATTGCTCTGGCTCAGGAAGGCGGTATCGGCTTTATCCACAAAAACATGTCCATTGA   540
CCGATAACGAGACCGAGTCCTTCCGCCATAGCCGAAATAGGTGTTTTTGTACAGGTAACT
```

FIG. 2B

```
       EcoRII
       BstNI  XmnI                              HinfI              AlwI
       |      |                                 |                  |
ACGCCAGGCAGAAGAAGTTCGCCGTGTGAAAAAACACGAATCTGGTGTGGTGACTGATCC       600
TGCGGTCCGTCTTCTTCAAGCGGCACACTTTTTTGTGCTTAGACCACACCACTGACTAGG HgaI
                         |
GCAGACTGTTCTGCCAACCACGACGCTGCGCGAAGTGAAAGAACTGACCGAGCGTAACGG      660
CGTCTGACAAGACGGTTGGTGCTGCGACGCGCTTCACTTTCTTGACTGGCTCGCATTGCC Cfr10I
                                                      |
TTTTGCGGGCTATCCGGTCGTTACCGAAGAAAACGAACTGGTGGGTATTATCACCGGTCG      720
AAAACGCCCGATAGGCCAGCAATGGCTTCTTTTGCTTGACCACCCATAATAGTGGCCAGC HgaI
                       Cfr10I           AhaII
                       |                |
TGACGTGCGTTTTGTTACCGACCTGAACCAGCCGGTTAGCGTTTACATGACGCCGAAAGA      780
ACTGCACGCAAAACAATGGCTGGACTTGGTCGGCCAATCGCAAATGTACTGCGGCTTTCT HgaI   BstEII
|      |
GCGTCTGGTCACCGTGCGTGAAGGTGAAGCCCGTGAAGTGGTGCTGGCAAAAATGCACGA      840
CGCAGACCAGTGGCACGCACTTCCACTTCGGGCACTTCACCACGACCGTTTTTACGTGCT MluI         HaeII
   AflIII       Eco47III           EcoRI                 BclI
   |            |                  |                     |
AAAACGCGTTGAAAAAGCGCTGGTGGTTGATGACGAATTCCACCTGATCGGCATGATCAC      900
TTTTGCGCAACTTTTTCGCGACCACCAACTACTGCTTAAGGTGGACTAGCCGTACTAGTG XmnI
|
CGTGAAAGACTTCCAGAAAGCGGAAGCTAAACCGAACGCCTGTAAAGACGAGCAAGGCCG      960
GCACTTTCTGAAGGTCTTTCGCCTTCGATTTGGCTTGCGGACATTTCTGCTCGTTCCGGC HgaI
                 BspMI                               HincII
                 |                                   | |
TCTGCGTGTTGGTGCAGCGGTTGGCGCAGGTGCGGGTAACGAAGAGCGTGTTGACGCGCT      1020
AGACGCACAACCACGTCGCCAACCGCGTCCACGCCCATTGCTTCTCGCACAACTGCGCGA PleI
        HincII         HinfI              DdeI
        |              |                  |
GGTTGCCGCAGGCGTTGACGTTCTGCTGATCGACTCCTCCCACGGTCACTCAGAAGGTGT      1080
CCAACGGCGTCCGCAACTGCAAGACGACTAGCTGAGGAGGGTGCCAGTGAGTCTTCCACA XhoII
                                     AlwI
                                     BspMII
                                     AccIII
                                     | |
ACTGCAACGTATCCGTGAAACCCGTGCTAAATATCCGGATCTGCAAATTATCGGCGGCAA      1140
TGACGTTGCATAGGCACTTTGGGCACGATTTATAGGCCTAGACGTTTAATAGCCGCCGTT
```

FIG. 2C

```
                HgiAI
             BspMI
         PstI Bsp1286                                      MseI
       PvuII ApaL1          AlwNI                           |
        | | |   |             |                             |
CGTGGCAACAGCTGCAGGTGCACGCGCTCTGGCAGAAGCTGGTTGCAGTGCGGTTAAAGT    1200
GCACCGTTGTCGACGTCCACGTGCGCGAGACCGTCTTCGACCAACGTCACGCCAATTTCA

EcoRII
      BstNI
      Sau96I
      Cfr13I                                     HgaI
      AsuI                                       AhaII
       | |                                        ||
CGGCATTGGCCCTGGCTCTATCTGTACAACTCGTATCGTGACTGGCGTCGGTGTTCCGCA    1260
GCCGTAACCGGGACCGAGATAGACATGTTGAGCATAGCACTGACCGCAGCCACAAGGCGT

Cfr10I
                                   EcoRII     NlaIV
                                   BstNI      BanI
             HgaI                    |         | |
              |                      |         | |
GATTACCGCTGTTGCTGACGCAGTAGAAGCCCTGGAAGGCACCGGTATTCCGGTTATCGC    1320
CTAATGGCGACAACGACTGCGTCATCTTCGGGACCTTCCGTGGCCATAAGGCCAATAGCG

TGATGGCGGTATTCGCTTCTCCGGCGACATCGCCAAAGCTATCGCCGCTGGCGCAAGCGC    1380
ACTACCGCCATAAGCGAAGAGGCCGCTGTAGCGGTTTCGATAGCGGCGACCGCGTTCGCG

NciI
          NlaIV                     HinfI      BcnI
            |                         |         |
GGTGATGGTAGGTTCCATGCTGGCGGGTACTGAAGAATCTCCGGGTGAAATCGAACTCTA    1440
CCACTACCATCCAAGGTACGACCGCCCATGACTTCTTAGAGGCCCACTTTAGCTTGAGAT Sau96I
    Cfr13I
    AsuI                    EcoRII
   EcoRII                   BstNI
   BstNI            NlaIV     |                    NlaIV
    | |              |        |                      |
CCAGGGCCGTTCTTACAAATCTTACCGTGGTATGGGTTCCCTGGGCGCGATGTCCAAAGG    1500
GGTCCCGGCAAGAATGTTTAGAATGGCACCATACCCAAGGGACCCGCGCTACAGGTTTCC NlaIV
                                               BanI
                                                |
TTCCTCTGACCGTTATTTCCAGAGCGATAACGCTGCCGACAAACTGGTGCCGGAAGGTAT    1560
AAGGAGACTGGCAATAAAGGTCTCGCTATTGCGACGGCTGTTTGACCACGGCCTTCCATA PflMI
                                      |
CGAAGGTCGCGTAGCCTATAAAGGTCGCCTGAAAGAGATCATTCACCAGCAGATGGGCGG    1620
GCTTCCAGCGCATCGGATATTTCCAGCGGACTTTCTCTAGTAAGTGGTCGTCTACCCGCC Cfr10I
                |
CCTGCGCTCCTGTATGGGTCTGACCGGCTGTGGTACTATCGACGAACTGCGTACTAAAGC    1680
GGACGCGAGGACATACCCAGACTGGCCGACACCATGATAGCTGCTTGACGCATGATTTCG
```

FIG. 2D

```
              SnaBI                      BsmI                         DraIII
                |                         |                             |
     GGAGTTTGTACGTATCAGCGGTGCGGGCATTCAGGAAAGCCACGTTCACGACGTGACCAT          1740
     CCTCAAACATGCATAGTCGCCACGCCCGTAAGTCCTTTCGGTGCAAGTGCTGCACTGGTA

NlaIV
            PleI                 Bsp1286
            HinfI                BanII    HinfI
              |                    ||       |
     TACTAAAGAGTCCCCGAACTACCGTCTGGGCTCCTGATTCTCTTCGCCCGACTTCATGTC          1800
     ATGATTTCTCAGGGGCTTGATGGCAGACCCGAGGACTAAGAGAAGCGGGCTGAAGTACAG HgaI           XmnI
                                                  |              |
     GGGCGATTTATATTATCTGTTTCACTTGCCTCGGAATAAGCGTCAATGACGGAAAACATT          1860
     CCCGCTAAATATAATAGACAAAGTGAACGGAGCCTTATTCGCAGTTACTGCCTTTTGTAA SfaNI
        SfaNI FokI                    DdeI                      BssHII
           |   ||                       |                          |
     CATAAGCATCGCATCCTCATTCTGGACTTCGGTTCTCAGTACACTCAACTGGTTGCGCGC          1920
     GTATTCGTAGCGTAGGAGTAAGACCTGAAGCCAAGAGTCATGTGAGTTGACCAACGCGCG FokI
                                         |
     CGCGTGCGTGAGCTGGGTGTTTACTGCGAACTGTGGGCGTGGGATGTGACAGAAGCACAA          1980
     GCGCACGCACTCGACCCACAAATGACGCTTGACACCCGCACCCTACACTGTCTTCGTGTT NciI
                                              BcnI
                                              Sau96I
                                              Cfr13I
                                              AsuI    ScaI
                                                 |      |
     ATTCGTGACTTCAATCCAAGCGGCATTATTCTTTCCGGCGGCCCGGAAAGTACTACTGAA          2040
     TAAGCACTGAAGTTAGGTTCGCCGTAATAAGAAAGGCCGCCGGGCCTTTCATGATGACTT Cfr10I
                                                  |
     GAAAACAGTCCGCGTGCGCCGCAGTATGTCTTTGAAGCAGGCGTACCGGTATTCGGCGTT          2100
     CTTTTGTCAGGCGCACGCGGCGTCATACAGAAACTTCGTCCGCATGGCCATAAGCCGCAA SphI      StyI
            NspHI     NcoI
              |         |
     TGCTATGGCATGCAGACCATGGCAATGCAGTTGGGCGGTCACGTTGAAGCCTCTAACGAA          2160
     ACGATACCGTACGTCTGGTACCGTTACGTCAACCCGCCAGTGCAACTTCGGAGATTGCTT BspMI
                     |
     CGTGAATTTGGCTACGCGCAGGTTGAAGTCGTAAACGACAGCGCACTGGTTCGCGGTATC          2220
     GCACTTAAACCGATGCGCGTCCAACTTCAGCATTTGCTGTCGCGTGACCAAGCGCCATAG SfaNI                                        FokI
              |                                            |
     GAAGATGCGCTGACCGCAGACGGTAAACCGCTGCTCGATGTCTGGATGAGCCACGGCGAT          2280
     CTTCTACGCGACTGGCGTCTGCCATTTGGCGACGAGCTACAGACCTACTCGGTGCCGCTA
```

FIG. 2E

```
AAAGTTACCGCTATTCCGTCCGACTTCATCACCGTAGCCAGCACCGAAAGCTGCCCGTTT    2340
TTTCAATGGCGATAAGGCAGGCTGAAGTAGTGGCATCGGTCGTGGCTTTCGACGGGCAAA

NciI      PleI
Bg1I                                          BcnI      HinfI
 |                                             |         |
GCCATTATGGCTAACGAAGAAAAACGCTTCTATGGCGTACAGTTCCACCCGGAAGTGACT    2400
CGGTAATACCGATTGCTTCTTTTTGCGAAGATACCGCATGTCAAGGTGGGCCTTCACTGA SphI
              NspHI
    EcoRII    FspI
    BstNI     AosI                    EcoRV
     |         | |                      |
CATACCCGCCAGGGTATGCGCATGCTGGAGCGTTTTGTGCGTGATATCTGCCAGTGTGAA    2460
GTATGGGCGGTCCCATACGCGTACGACCTCGCAAAACACGCACTATAGACGGTCACACTT HgaI                            FokI
    AhaII            SfaNI          SfaNI         BspMI
     |                 |             | |           |
GCCCTGTGGACGCCAGCGAAAATTATCGACGATGCTGTAGCTCGCATCCGCGAGCAGGTA    2520
CGGGACACCTGCGGTCGCTTTTAATAGCTGCTACGACATCGAGCGTAGGCGCTCGTCCAT FokI                         HinfI
          |                             |
GGCGACGATAAAGTCATCCTCGGCCTCTCTGGTGGTGTGGATTCCTCCGTAACCGCAATG    2580
CCGCTGCTATTTCAGTAGGAGCCGGAGAGACCACCACACCTAAGGAGGCATTGGCGTTAC SalI
                                      HincII
                                      AccI
                                        |
CTGCTGCACCGCGCTATCGGTAAAAACCTGACTTGCGTATTCGTCGACAACGGCCTGCTG    2640
GACGACGTGGCGCGATAGCCATTTTTGGACTGAACGCATAAGCAGCTGTTGCCGGACGAC AlwNI
           BspMI                                     MseI
            ||                                        |
CGCCTCAACGAAGCAGAGCAGGTTCTGGATATGTTTGGCGATCACTTTGGTCTTAACATT    2700
GCGGAGTTGCTTCGTCTCGTCCAAGACCTATACAAACCGCTAGTGAAACCAGAATTGTAA BspMII
                              HaeII                  AccIII
          Cfr10I               Eco47III              AlwI
            |                    |                    | |
GTTCACGTACCGGCAGAAGATCGCTTCCTGTCAGCGCTGGCTGGCGAAAACGATCCGGAA    2760
CAAGTGCATGGCCGTCTTCTAGCGAAGGACAGTCGCGACCGACCGCTTTTGCTAGGCCTT
```

FIG. 2F

```
                                              HaeII
                                              Eco47III
                                              |
GCAAAACGTAAAATCATCGGTCGCGTTTTCGTTGAAGTATTCGATGAAGAAGCGCTGAAA    2820
CGTTTTGCATTTTAGTAGCCAGCGCAAAAGCAACTTCATAAGCTACTTCTTCGCGACTTT

NlaIV
                   BanI
                   Bsp1286                         HinfI    AhaII
                   | |                             |        |
CTGGAAGACGTGAAGTGGCTGGCGCAGGGCACCATCTACCCTGACGTTATCGAATCTGCG    2880
GACCTTCTGCACTTCACCGACCGCGTCCCGTGGTAGATGGGACTGCAATAGCTTAGACGC DraIII
HgaI       Cfr10I     AflIII       PflMI
|          |          |            ||
GCGTCTGCAACCGGTAAAGCACACGTCATCAAATCTCACCACAACGTGGGCGGCCTGCCG    2940
CGCAGACGTTGGCCATTTCGTGTGCAGTAGTTTAGAGTGGTGTTGCACCCGCCGGACGGC EcoRII
           BstNI
        Sau96I
        BaeI
        Cfr13I
        AsuI
        | |
AAAGAGATGAAGATGGGCCTGGTTGAACCGCTGAAAGAGCTGTTCAAAGACGAAGTGCGT    3000
TTTCTCTACTTCTACCCGGACCAACTTGGCGACTTTCTCGACAAGTTTCTGCTTCACGCA Sau96I
                                                       Cfr13I
                                                       AvaII
                                                       AsuI
                                                       NlaIV
                                                       NciI
                                                       BcnI
                                                       XmaI
                          Sau96I                       SmaI
                          BaeI                         NciI
                          Cfr13I                       BcnI
                          AsuI    SplI   NspHI         AvaI
                          |       |      |             || ||
AAGATTGGTCTGGAGCTGGGCCTGCCGTACGACATGCTGTACCGTCACCCGTTCCCGGGA    3060
TTCTAACCAGACCTCGACCCGGACGGCATGCTGTACGACATGGCAGTGGGCAAGGGCCCT
```

FIG. 2G

```
     StyI
    StuI
   EaeI
  PflMI
  EcoRII
  BstNI                                        ScaI        BspMI
  | | |                                         |           |
  CCAGGCCTTGGCGTTCGTGTTCTGGGTGAAGTGAAGAAAGAGTACTGTGACCTGCTGCGC   3120
  GGTCCGGAACCGCAAGCACAAGACCCACTTCACTTCTTTCTCATGACACTGGACGACGCG

Sau96I
                                   Cfr13I
           HgaI                    AvaII                     EcoRII
           AhaII                   AsuI        Tth111I       BstNI
            |                        |            |           |
  CGTGCTGACGCCATCTTCATTGAAGAACTGCGTAAAGCGGACCTGTACGACAAAGTCAGC   3180
  GCACGACTGCGGTAGAAGTAACTTCTTGACGCATTTCGCCTGGACATGCTGTTTCAGTCG

Cfr10I
                 |
  CAGGCGTTCACTGTGTTCCTGCCGGTACGTTCCGTTGGCGTAATGGGCGATGGTCGTAAG   3240
  GTCCGCAAGTGACACAAGGACGGCCATGCAAGGCAACCGCATTACCCGCTACCAGCATTC

TATGACTGGGTTGTCTCTCTGCGTGCTGTCGAAACCATCGACTTTATGACCGCACACTGG   3300
  ATACTGACCCAACAGAGAGACGCACGACAGCTTTGGTAGCTGAAATACTGGCGTGTGACC

SfaNI    SplI
       |       |
  GCGCATCTGCCGTACGATTTCCTCGGTCGCGTTTCCAACCGCATTATCAATGAAGTGAAC   3360
  CGCGTAGACGGCATGCTAAAGGAGCCAGCGCAAAGGTTGGCGTAATAGTTACTTCACTTG

PflMI
                                                         |
  GGTATTTCCCGCGTGGTGTATGACATCAGCGGCAAGCCGCCAGCTACCATTGAGTGGGAA   3420
  CCATAAAGGGCGCACCACATACTGTAGTCGCCGTTCGGCGGTCGATGGTAACTCACCCTT

TGATTTGACCCTGCACTATGAATGAACAAAACCCTCTGTTACTACAGAGGGTTTTTTATC   3480
  ACTAAACTGGGACGTGATACTTACTTGTTTTGGGAGACAATGATGTCTCCCAAAAAATAG

AseI MseI
              ClaI  MseI       PvuII
                |    ||          |
  TTCAAGAATTATAGGATTGAAGTTACTAACATCGATTAATTAAACCAGCTG   3531
  AAGTTCTTAATATCCTAACTTCAATGATTGTAGCTAATTAATTTGGTCGAC
```

GUA MUTANTS OF SHIGELLA SPP. AND VACCINES CONTAINING THE SAME

FIELD OF THE INVENTION

The present invention relates to gua mutants of Shigella spp., and vaccines against shigellosis containing the same, live vector vaccines containing the same, and DNA-mediated vaccines containing the same.

BACKGROUND OF THE INVENTION

I. Shigella spp. and Shigellosis

The genus Shigella is divided into four species or groups: *S. dysenteriae* (group A), *S. flexneri* (group B), *S. boydii* (group C) and *S. sonnel* (group D). The first three groups are further divided, based on their O antigens, into multiple serotypes and subtypes, totaling more than three dozen, whereas only a single serotype of *S. sonnei* is recognized. Humans are the natural host and reservoir for Shigella, although certain serotypes have also become an endemic problem of primate colonies in captivity.

Shigella infections are a major public health problem among young children in less-developed countries and among travelers from industrialized countries who visit developing countries (World Health Organization, *Bull. WHO*, 65:17–25 (1987); Ferreccio et al, *Am. J. Epidemiol.*, 134:614–627 (1991); and DuPont et al, *N. Engl. J. Med.*, 285:1520–1521 (1976)). However, Shigella infections remain a public health problem in certain high-risk groups in industrialized countries as well. A feature of the pathogenesis of shigellosis that greatly influences the epidemiology of this enteric infection is the fact that as few as 10 wild-type Shigella organisms ingested by a susceptible host, without buffering of gastric acid, can lead to full-blown shigellosis (Levine et al, *J. Infect. Dis.*, 127:261–270 (1973)). Thus, Shigella infections are readily transmitted from person-to-person by direct contact involving fecally-contaminated fingers or by contaminated fomites, in addition to less common transmission by contaminated food and water vehicles. Transmission of shigellosis is favored wherever personal hygiene is compromised. This explains why Shigella infections persist as a public health problem in certain high-risk groups in industrialized countries, such as inmates of custodial institutions for the mentally-retarded (DuPont et al, *Am. J. Epidemiol.*, 92:172–179 (1970); Levine et al, *Am. J. Epidemiol.*, 99:30–36 (1974a); Levine et al, *J. Pediatr.*, 84:803–806 (1974b); and Levine et al, *Am. J. Epidemiol.*, 104:88–92 (1976)), and the psychotic, and toddlers and pre-school children who attend day care centers (Pickering et al, *J. Pediatr.*, 99:51–56 (1981)), all populations in whom personal hygienic practices are primitive or compromised.

*S. dysenteriae, S. flexneri* and *S. boydii* are mainly found in less-developed countries (Ferreccio et al, supra; Khan et al, *Int. J. Epidemiol.*, 14:607–613 (1985); and Echeverria et al, *Rev. Infect. Dis.*, 13:S220–S225 (1991)), while *S. sonnei* is the predominant species that affects industrialized country populations, and is an important cause of travelers' shigellosis (DuPont et al, (1976) supra; DuPont et al, (1970) supra; Levine et al, (1974a) supra; Levine et al, (1974b) supra; Levine et al, (1976) supra; and Pickering et al, supra).

In non-immune populations, whether travelers or young children, in less-developed countries, the clinical illness caused by Shigella tends to be particularly severe, characterized by high fever, disabling abdominal cramps, malaise, diarrhea, and finally dysentery (stools containing gross blood and mucus) accompanied by tenesmus. Throughout the developing world, in tropical, sub-tropical and temperate climates, Shigella are isolated from stool cultures of approximately 5–15% of young children less than five years of age who seek medical care at health care facilities with a chief complaint of diarrheal illness or dysentery; isolation rates from controls without diarrhea are in the range of 1–3% (Ferreccio et al, supra; and Stoll et al, *J. Infect. Dis.*, 146:177–199 (1982)). Recent epidemiologic studies carried out by the Centers for Vaccine Development (CVD) in a peri-urban slum in Santiago, Chile show that shigellosis persists as an important and common pediatric enteric infection in low socioeconomic communities even when bacteriologically monitored water is provided to households (Ferreccio et al, supra).

One serotype, *S. dysenteriae* 1, the so-called Shiga bacillus, is unique among Shigella because of the severity of illness that it causes, its ability to spread in large pandemics involving many countries extending over many years (Gangarosa et al, *J. Infect. Dis.*, 122:181–190 (1970); Rahaman et al, *J. Infect. Dis.*, 132:15–19 (1975); Mata et al, *J. Infect. Dis.*, 122:170–180 (1970); and Bennish et al, *Rev. Infect. Dis.*, 13:S245–S251 (1991)), and its propensity to harbor plasmids carrying resistance to multiple clinically-important antibiotics (Mata et al, supra; Rahaman et al, supra; and Taylor et al, *Am. J. Trop. Med. Hyg.*, 40:77–85 (1989)). Not only does uncomplicated Shiga dysentery tend to be a severe, sometimes fatal illness (Mata et al, supra; Rahaman et al, supra; Taylor et al, supra; and Bennish et al, supra), but it is often accompanied by life-endangering complications, such as the hemolytic-uremic syndrome and acute hypoproteinemia (Mata et al, supra; Rahaman et al, supra; and Taylor et al, supra).

The World Health Organization (WHO) has made the development of effective vaccines to prevent Shigella disease a high priority (World Health Organization, (1987) supra). A high priority to developing new Shigella vaccines was similarly given by the Institute of Medicine (Institute of Medicine, In: *New Vaccine Development: Establishing priorities. II. Diseases of Importance in Developing Countries*, Washington, D.C. National Academy Press (1986)). Target populations for the use of Shigella vaccines include infants and toddlers in developing countries, travelers who visit less-developed areas of the world, residents of custodial institutions, and young children who attend large pediatric day care centers in industrialized countries.

II. Experimental and Epidemiological Observations on Protective Immunity to Shigella It is clear from experimental challenge of volunteers (DuPont et al, *J. Infect. Dis.*, 125:12–16 (1972); and Herrington et al, *Vaccine*, 8:353–357 (1990)), and monkeys (Formal et al, *J. Infect. Dis.*, 164:533–537 (1991)), and from epidemiologic studies in which cohorts of children are prospectively followed (Ferreccio et al, supra), that an initial clinical infection due to Shigella gives substantial protection against clinical illness upon subsequent exposure to the homologous serotype. Consequently, and given the relatively large number of Shigella serotypes, several groups of investigators have explored the possibility of immunizing against more than one serotype at the same time and/or conferring cross-protective immunity against other serotypes.

A. Polyvalent Shigella Vaccines

In the 1940's, mice and children were immunized with a polyvalent *S. flexneri* vaccine (Cooper et al, *J. Immunol.*, 58:361–368 (1948); and Cooper et al, *J. Immunol.*, 61:209–219 (1949)). The vaccine consisted of a mixture of parenterally administered, inactivated, *S. flexneri* strains of the serotypes II, III and VII (later respectively known as serotypes 2, 3 and X). A protective immune response, determined by the passive protection of mice by sera, indicated a strong immune response and increase in protective power against wild-type strains of the same serotype (Cooper et al, (1949) supra).

Various attenuated strains were also constructed by conjugating virulent Shigella with an Hfr strain of E. coli K12. Two oral doses of a polyvalent vaccine that included the serotypes attenuated S. flexneri 1b, S. flexneri 2a, S. flexneri 3 and S. sonnei I were able to confer protection to monkeys challenged with the homologous serotypes, but did not protect against infection with S. flexneri 6 (Formal et al, J. Bacteriol., 92:17–22 (1966)). Unfortunately, these hybrids constructed in the 1960's were still able to produce a positive Sereny test in guinea pigs, and therefore they are not considered to be sufficiently attenuated for studies in volunteers.

A few years later, in Yugoslavia, the results of immunizing volunteers (soldiers) with a combination of streptomycin-dependent (SmD), non-virulent S. flexneri strains, serotypes 2a and 3 was reported (Mel et al, Bull. WHO, 39:375–380 (1968)). This study demonstrated that oral administration of the 2 serotypes combined did not interfere with the immune response in humans against the individual serotypes.

The above studies suggest that protection against multiple Shigella serotypes with an oral polyvalent Shigella vaccine is feasible.

B. Cross-Protection Among Shigella Serotypes

It is well-accepted that protective immunity against Shigella spp. is primarily directed against their O antigen, and there are no significant cross-reactions among the organisms of Shigella groups A, C, and D (Robbins et al, Clin. Infect. Dis., 15:346–361 (1992)). Therefore, it is not realistic to attempt to protect against all of the 32 serotypes that are included in these three groups. Fortunately, only 2 serotypes are presently considered to be of public health importance. These are S. dysenteriae type 1 (Gangarosa et al, supra; Rahaman et al, supra; Mata et al, supra; and Bennish et al, supra), and S. sonnei (DuPont et al, (1976) supra; DuPont et al, (1970) supra; Levine et al, (1974a) supra; Levine et al, (1974b) supra; Levine et al, (1976) supra; and Pickering et al, supra). In contrast, there are major cross-reactions among the multiple serotypes that are included in the Shigella group B (S. flexneri) (Edwards et al, In: Identification of Enterobacteriacaea., 3rd Ed., Burgess Publishing Co., Minneapolis, Minn. (1972)), and data from experimental observations (Weil et al, J. Immunol., 51:301–305 (1945); and Sereny et al, Acta Microbiol. Acad. Sci. Hung., 18:239–245 (1971)), and clinical trials (Cooper et al, (1949) supra) support that cross-protection may be conferred by some of the members of this group against other serotypes of the same group. It was reported 50 years ago that mice immunized with S. flexneri III-Z (later known as 3a) conferred cross-protection against challenge with wild-type S. flexneri I–III (later known as 1b), but much less protection against S. flexneri II-W and VI-Boyd 88 (later known as 2a and 6, respectively) (Weil et al, supra). It has also been reported that serum from children immunized with S. flexneri II, III and VII (later known as 2, 3 and X, respectively) protected mice against the homologous serotypes, and against the heterologous S. flexneri I (later known as 1), but not against serotype VI (later known as 6) (Cooper et al, (1949) supra). Further, it was reported that immunization of guinea pigs with S. flexneri 4b protected them against challenge with wild-type S. flexneri 4b and 3a (Sereny et al, supra). Unfortunately, other reports on this respect are more difficult to analyze because of the lack of identification of the specific subserotypes involved in the studies.

All of the Shigellae belonging to this group (with the exception of serotype 6) have some degree of antigenic relatedness given by a common repeating tetrasaccharide unit: α-L-Rhap1→2-α-L-Rhap1→3-α-L-Rhap1→3β-D-GlcpNAc1; to which α-D-glucopyranosyl and O-acetyl groups are added, providing the basis for their serotype (1–5b, X and Y) and subserotype (a, b, c) classification (Carlin et al, Eur. J. Biochem., 139:189–194 (1984); and Edwards et al, supra). This common O antigen structure served as the rationale to construct a vaccine candidate based on an attenuated strain of S. flexneri Y (strain SFL114) (Lindberg et al, Microb. Pathog., 8:433–440 (1990)). It has been reported that monkeys immunized with strain SFL114 were protected against wild-type strains of the homologous serotype Y and the heterologous 1b and 2a (Karnell et al, Vaccine, 10:167–174 (1992)). However, these results were not found to be reproducible in the guinea pig model (Hartman et al, Infect. Immun., 59:4075–4083 (1991)).

The fact that cross-protection between all S. flexneri serotypes has not been found is not surprising given the variability conferred by the antigenic factors responsible for their type (factors I–VI) and subserotype (factors 3, 4, 6, 7 and 8) classification (Edwards et al, supra). In this regard, quantitative studies of serological cross-reaction among O antigens of S. flexneri have revealed that most of the antibodies are directed against subserotype factors and not the type antigen. Therefore, the cross-protection that has been observed between S. flexneri of the serotypes 3a and 1b (Weil et al, supra), and 4b and 3a (Sereny et al, supra), may be due to the fact that they share the subserotype antigenic factor 6.

In summary, the data generated over 3 decades suggest three approaches to generate a vaccine able to protect against dysentery caused by S. flexneri:

(i) to make a vaccine based on the antigenic cross-reaction provided by the S. flexneri tetrasaccharide unit; this approach (Lindberg et al, supra), may not succeed given the multiple reports of failure of cross-protection among different S. flexneri serotypes;

(ii) to construct a polyvalent vaccine based on a mixture of strains that include all (or the most epidemiologically relevant) S. flexneri serotypes; this approach is likely to provide protective immunity to the individual components of the vaccine (Mel et al, (1968) supra; and Formal et al, (1966) supra); however, there are 15 serotypes in the S. flexneri group, and the most relevant in a specific geographic area may not be in another;

(iii) to construct a polyvalent vaccine based on serotypes that carry some of the most prevalent type factors and all the subserotype antigenic factors. The rationale for such a vaccine would be that overall, the multiple serotypes of S. flexneri (group B) are the most common cause of shigellosis in developing countries. A unique characteristic of this group is that the structure of their O antigen share a common repeating tetrasaccharide unit upon which α-D-glucopyranosyl and O-acetyl groups are attached. Based on the specificity provided by those added molecules, Group B is divided into serotypes (i.e., 1–6, X and Y) and subserotypes (i.e., a, b and c). The identification of each serotype is given by specific agglutination with antiserum directed against the type factors and the subserotype factors. Some experimental observations indicate the possibility of cross-protection among serotypes of the S. flexneri group that share subserotype antigenic complexes (Weil et al, supra; and Sereny et al, supra). In using this approach, the selection of the parents of S. flexneri mutants of the present invention is based on their prevalence, as well as their potential to cross-react with other serotypes and subserotypes of this species. Exception to this rationale was the *S. flexneri* 6 candidate, which as shown in Table 1 below, is singly represented in its specific serotype, and does not share group factors with other *S. flexneri*. Therefore, attenuated *S. flexneri* 6 can be included with the *S. flexneri* mutants of the present invention to protect specifically against *S. flexneri* 6 wild-type strains. In contrast, as shown in Table 1 below, by including attenuated strains of *S. flexneri* 2a and *S. flexneri* 3a, with the *S. flexneri* mutants of the present invention, one may be immunizing against the type and/or subserotype antigens represented in the rest of the *S. flexneri* serotypes. Therefore, by combining *S. flexneri* 2a (type factor II; subserotype factors: 3 and 4) and *S. flexneri* 3a (type factor III; subserotype factors: 6, 7 and 8), immunity against prevalent serotypes *S. flexneri* 2b (type factor II; but subtype factors: 7 and 8) and *S. flexneri* 3b (type factor III, but subtype factors: 3, 4 and 6), may be enhanced.

supra; and Levine et al, (1972) supra), but efficacy was variable, depending on the type of population vaccinated (Levine et al, (1974b) supra; and Levine et al, (1976) supra). Another vaccine candidate strain that was developed in the 1960s that also was well-tolerated and protective was $T_{32}$ (Istrati et al, *Arch. Roumaines. Pathol. Exp. Microbiol.*, 24:677–686 (1965)), a *S. flexneri* 2a mutant selected after 32 passages on agar. However, there are drawbacks to these non-invasive SmD vaccines, including the need for multiple doses (Levine et al, (1974b) supra; Levine et al, (1976) supra; Mel et al, (1968) supra; Mel et al, (1971) supra; and Mel et al, (1974) supra), the large number of vaccine organisms required per dose (which affect the cost), the occurrence of vomiting (possible due to the large number of organisms) (Mel et al, (1968) supra; Mel et al, (1971) supra; Mel et al, (1974) supra; and Levine et al, (1972) supra), the detection of streptomycin-independent revertants in one lot of *S. sonnei* vaccine (Levine et al, *J. Infect. Dis.*, 131:704–707 (1975)), and the need for a booster dose at one year to maintain protection (Mel et al, (1974) supra).

Over the next 15 years, several new generations of candidate Shigella vaccines were developed in an attempt to improve on the SmD and $T_{32}$ vaccines. These included:

TABLE 1

| | Cross-reactivity with *S. flexneri*: | | | | | | | | | | | | | | |
|---|---|---|---|---|---|---|---|---|---|---|---|---|---|---|---|
| Vaccine/O Antigen | 1a | 1b | 2a | 2b | 3a | 3b | 3c | 4a | 4b | 4c | 5a | 5b | 6 | X | Y |
| CVD 1205 | | | | | | | | | | | | | | | |
| Type factor II | | | + | + | | | | | | | | | | | |
| Group factors 3, 4 | + | | + | | | + | | + | | | + | | | | + |
| CVD 1211 | | | | | | | | | | | | | | | |
| Type factor III | | | | | + | + | + | | | | | | | | |
| Group factors 6 | | + | | | + | + | + | | + | | | | | | |
| Group factors 7, 8 | | | | + | + | | | | | + | | + | | + | |
| CVD 1215 | | | | | | | | | | | | | | | |
| Type factor VI | | | | | | | | | | | | | + | | |
| Group factors -- | | | | | | | | | | | | | | | |

III. Earlier Generations of Shigella Vaccines

Inactivated Shigella bacteria administered parenterally as whole cell vaccines have failed to protect monkeys (Formal et al, *Proc. Soc. Exp. Biol.* (N.Y.), 125:347–349 (1967)), or volunteers (Shaughnessy et al, *JAMA*, 132:362–368 (1946)), against experimental challenge. Also, these vaccines did not protect children from natural challenge in endemic situations (Higgins et al, *Am. J. Trop. Med. Hyg.*, 4:281–288 (1955)). In contrast, attenuated Shigella strains utilized as live oral vaccines have significantly protected volunteers against experimental shigellosis (DuPont et al, (1972) supra; and Black et al, J. Infect. Dis., 155:1260–1265 (1987)), and populations in endemic areas against natural endemic challenge (Mel et al, (1968) supra; Mel et al, *Bull. WHO*, 45:457–464 (1971); and Mel et al, *Acta Microbiol. Acad. Sci. Hung.*, 21:109–114 (1974)). The standard for what live oral Shigella vaccines can accomplish is best exemplified by experiences with the SmD mutants (Mel et al, (1968) supra; Mel et al, (1971) supra; and Mel et al, (1974) supra). In the early 1970s, the U.S. Public Health Service sponsored studies of the SmD vaccines as a possible control measure against custodial shigellosis (Levine et al, (1974b) supra; Levine et al, (1976) supra; and Levine et al, *Am. J. Epidemiol.*, 96:40–49 (1972)). These vaccine strains were well-tolerated in highly debilitated subjects living in custodial care (Levine et al, (1974b) supra; Levine et al, (1976)

(1) non-invasive *E. coli* that express *S. flexneri* 2a group- and type-specific O antigens (Levine et al, *J. Infect. Dis.*, 136:577–582 (1977));

(2) attenuated *Salmonella typhi* strain Ty21a expressing the O antigen of *S. sonnei* (Formal et al, *Infect. Immun.*, 34:746–750 (1981));

(3) *E. coli* K12 with an *S. flexneri* invasiveness plasmid, genes to express *S. flexneri* 2a O antigen (Formal et al, *Infect. Immun.*, 46:465–469 (1984)), and a mutation in the aroD gene (Newland et al, *Vaccine*, 10:766–776 (1992));

(4) *S. flexneri* Y and *S. flexneri* 2a harboring mutations in genes (aroA, aroD or both) in the aromatic amino acid biosynthesis pathway (Lindberg et al, supra; and Verma et al, *Vaccine*, 9:6–9 (1991)); and (5) *S. flexneri* harboring mutations in the chromosomal gene (iuc) that encodes the siderophore aerobactin, and in the plasmid gene virG (i.e., icsA) (Sansonetti et al, *Vaccine*, 7:443–450 (1989)).

An important observation made with the *E. coli* K-12/invasiveness plasmid/O antigen/aroD construct and with aro mutants of Shigella is that when large numbers of vaccine organisms ($2.5\times10^9$–$10^{10}$) are fed to immunologically-naive volunteers, adverse reactions are seen (Kotloff et al, *Infect. Immun.*, 60:2218–2224 (1992); Li et al, *Vaccine*, 11:180–189 (1993); and Karnell et al. *Rev. Infect. Dis.*, 4(Suppl 13):S357–S361 (1991)). The observed adverse reactions include occasional fever and dysentery, but most commonly diarrhea (Kotloff et al. supra; Li et al. supra; and Karnell et al. (1991) supra).

In summary, the data generated during the past 3 decades by experimental Shigella vaccine candidates indicates four important lessons to be applied to continuing Shigella vaccine development efforts:

(i) If wild-type Shigella can be sufficiently attenuated, safe and effective vaccines can result (Mel et al. (1968) supra; Mel et al. (1971) supra; Mel et al. (1974) supra; Levine et al. (1972) supra; and Istrati et al. supra);

(ii) Heretofore, the well-tolerated live vaccines have required the administration of multiple doses in order to provide protection (Mel et al. (1968) supra; Mel et al. (1971) supra; Mel et al. (1974) supra; Levine et al. (1972) supra; and Istrati et al. supra);

(iii) Vaccines based on the use of modified *E. coli* as live vectors have either been well-tolerated but non-protective (in volunteer studies) (Levine et al. (1977) supra), or have been partially protective, but less well-tolerated (Kotloff et al. supra); and (iv) Attempts, so far, to prepare more immunogenic (potentially single-dose) attenuated Shigella vaccines have not been able to uncouple residual reactogenicity from enhanced immunogenicity (Li et al. supra; and Karnell et al. (1991) supra).

IV. Attenuated Oral Vaccine Candidates ΔvirG, ΔaroA *S. flexneri* 2a Strain CVD 1203

Encouraged by the successful attenuation of Salmonella by mutations in the aromatic metabolic pathway (Hoiseth et al. *Nature*, 292:238–239 (1981); Robertson et al. *Infect. Immun.*, 41:742–750(1983); and Hone et al. *Vaccine*, 9:810–816 (1991)), aro⁻ auxotrophic mutants of Shigella spp. were constructed, and their attenuation demonstrated in animal models (Lindberg et al. *Vaccine*, 6:146–150 (1988); Karnell et al. (1992) supra; and Lindberg et al. (1990) supra). The consequences of the interruption of the aromatic metabolic pathway in Shigella are auxotrophy for PABA (see FIG. 1), which is not found in mammalian cells, and consequently the intracellular growth of the mutant is severely hindered. However, some of these aro⁻ auxotrophic strains have exhibited reactogenicity when administered in high doses to volunteers (Li et al. supra; and Karnell et al. *Vaccine*, 13:88–99 (1995)). In order to enhance the attenuation conferred by the aro mutations, a specific, in-frame, deletion mutation has been introduced in the virulence gene virG of ΔaroA *S. flexneri* 2a (strain CVD 1201), resulting in double mutant ΔaroA, ΔvirG strain CVD 1203 (Noriega et al. *Infect. Immun.*, 62:5168–5172 (1994)). These specific, in-frame deletion mutations were performed by allelic exchange recombination of the modified genes with their wild-type counterparts with the use of suicide vectors in virulent strain 2457T (Noriega et al. supra). The resultant ΔvirG, ΔaroA *S. flexneri* 2a vaccine strain CVD 1203, caused an early (first 24 h), mild, short-lived (resolved by 48 h), inflammatory response in the conjunctiva of guinea pigs (Sereny test) at high doses ($10^9$ cfu) (X10 $ID_{100}$). After oral immunization, CVD 1203 elicited an anti-*S. flexneri* 2a LPS secretory-IgA (SIgA) immune response that protected guinea pigs against subsequent challenge with the wild-type homologous strain (Noriega et al. supra).

Recently, strain CVD 1203 was tested in a phase I safety/immunogenicity study in volunteers at the CVD (Kotloff et al. In: *Program and Abstracts, 35th Interscience Conference on Antimicrobial Agents and Chemotherapy* (ICAAC) G26, page 163 (Abstract) (1995)). While an oral dose of $1.0 \times 10^5$ colony forming units (cfu) of the virulent parent strain 2457T caused overt illness in 85%–90% of volunteers, $1.0 \times 10^9$ cfu of strain CVD 1203 produced a short lived (<24 h), markedly attenuated illness (defined as the presence of fever, diarrhea and/or dysentery). Furthermore, a clear-cut dose response was detected, with illness developing in 7 out of 11 volunteers (72%), 3 out of 11 volunteers (18%), and 0 out of 10 volunteers (0%) after a single dose of $1.5 \times 10^9$ cfu, $1.5 \times 10^8$ cfu, and $1.2 \times 10^6$ cfu of CVD 1203, respectively. The reactogenicity of ΔvirG, ΔaroA CVD 1203 at high doses was similar to that reported for in Swedish and Vietnamese volunteers who received aroD mutants of *S. flexneri* Y and *S. flexneri* 2a (Li et al. supra; and Karnell et al. (1995) supra).

Nonetheless, strain CVD 1203 was immunogenic at doses of $1.0 \times 10^6$ cfu, where illness was not seen. Table 2 below compares the anti-LPS secretory-IgA SIgA antibody secreting cell (ASC) response 7 days following vaccination with an *E. coli* K12/*S. flexneri* 2a vaccine hybrid, strain EcSf2a-2 (Kotloff et al. (1992) supra) or with CVD 1203 (extemporaneous studies). It is clear from these clinical trials with CVD 1203, that mutations in aroA and virG do not sufficiently attenuate wild-type *S. flexneri* 2a to provide the proper balance of clinical acceptability and immunogenicity.

TABLE 2

IgA ASC Response in Adult Volunteers Following Challenge with Wild-type *S. flexneri* 2a or Immunization with Live Oral Vaccines

| Immunizing Vaccine Regimen | N | IgA ASCs: Responders | ASCs* | Efficacy |
|---|---|---|---|---|
| Wild-type EcSf2a-2 | 11 | 100% | 129 | 70% |
| $2.0 \times 10^9$ cfu × 3 | 15 | 87% | 59 | 48% |
| $5.0 \times 10^8$ cfu × 2 | 22 | 64% | 18 | 27% |
| $2.0 \times 10^9$ cfu × 3 CVD 1203 (single dose): | 20 | 45% | 21 | 0% |
| $10^9$ cfu | 11 | 100% | 169 | ? |
| $10^8$ cfu | 11 | 91% | 61 | ? |
| $10^6$ cfu | 10 | 60% | 69 | ? |

*Geometric mean number of ASCs among responders

In previous protection studies performed at the CVD with strain EcSf2a-2, the protective efficacy following challenge of volunteers with virulent *S. flexneri* 2a demonstrated a trend in which the height of the anti-LPS SIgA ASC response, and the proportion of subjects responding correlated with protective immunity (Kotloff et al. (1992) supra). As shown, in Table 2 above, one dose of CVD 1203 compares very favorably to even three doses of EcSf2a-2.

V. Live Vaccines

A. Attenuated Shigella Strains as Live Vector Vaccines that Express Foreign Genes from other Pathogens Live vector vaccines, also called "carrier vaccines" and "live antigen delivery systems", comprise an exciting and versatile area of vaccinology (Levine et al. *Microecol. Ther.*, 19:23–32 (1990); Morris et al. *Gastroenterol.*, 103:699–702 (1992); Barletta et al. *Res. Microbiol.*, 141:931–940 (1990); Dougan et al. *Para. Immunol.*, 9:151–160 (1987); and Curtiss et al. *Curr. Top. Microbiol. Immunol.*, 146:35–49 (1989)). In this approach, a live viral or bacterial vaccine is modified so that it expresses protective foreign antigens of another microorganism, and delivers those antigens to the immune system, thereby stimulating a protective immune response. Live bacterial vectors that are being promulgated include, among others, attenuated Salmonella (Levine et al. (1990) supra; Morris et al. supra; Dougan et al. supra; and Curtiss et al. supra), Bacille Calmette Guerin (Barletta et al. supra), *Yersinia enterocolitica* (Van Damme et al. *Gastroenterol.*, 103:520–531 (1992)), *V. cholerae* O1 (Viret et al. *Mol. Microbiol.*, 7:239–252 (1993)) and *E. coli* (Hale, *Res. Microbiol.*, 141:913–919 (1990)). Each has certain advantages and some disadvantages. The use of attenuated organisms as live vectors/vaccines expressing protective antigens of relevant pathogens is well-known. Attenuated Shigella are also attractive candidates for live vector vaccines. These attenuated Shigella strains are administered orally, colonize the gut-associated lymphoid tissue (sansonetti et al. *Vaccine*, 9:416–422 (1991); and Wassef et al. *Infect. Immun.*, 57:858–863 (1989)), and elicit a relatively broad immune response that includes mucosal SIgA, serum antibodies, cell-mediated immune responses and a form of antibody-dependent cellular cytotoxicity (Kotloff et al. (1992) supra; Persson et al. *Infect. Immun.*, 52:834–839 (1986); Oaks et al. *Infect. Immun.*, 53:57–63 (1986); Van de Verg et al. *Infect. Immun.*, 58:2002–2004 (1990); Lowell et al. *J. Immunol.*, 125:2778–2784 (1980); Cohen et al. *J. Clin. Microbiol.*, 27:162–167 (1989); and Oberhelman et al. *Infect. Immun.*, 59:2341–2350 (1991)). Moreover, Shigella, which shares a high degree of homology with *E. coli*, is readily manipulated genetically.

Oral vaccines against a variety of infectious diseases can be developed by introducing and stably expressing foreign genes encoding protective antigens in a Shigella live vector strains. In pursuing this approach, a ΔvirG, ΔaroA *S. flexneri* 2a strain CVD 1203 expressing CFA/I fimbriae and CS3 fibrillae of enterotoxigenic *E. coli* (ETEC) has been constructed as a vaccine/vector prototype, and tested in a guinea pig animal model (Noriega et al, *Infect. Immun.*, 64:23–27 (1996)). The results are shown in Table 3 below.

TABLE 3

Reciprocal Geometric Mean Titers of IgA Anti-*S. flexneri* 2a LPS or ETEC CFA/I and CS3 in Tears of Guinea Pigs after Two Doses[a] of CVD 1203 (pJGX15A, pACCS3-1)

| | Anti-LPS Titer on Day: | | Anti-CFA/I Titer on Day: | | Anti-CS3 Titer on Day: | |
|---|---|---|---|---|---|---|
| Route | 0 | 28 | 0 | 28 | 0 | 28 |
| o.g.[a] | 20 | 201 | 20 | 844 | 40 | 67 |
| i.n.[b] | 20 | 1280 | 20 | 1280 | 40 | 5120 |

[a]Orogastric dose: $3.0 \times 10^{10}$ at days 0 and 14
[b]Intranasal dose: $3.0 \times 10^{9}$ at days 0 and 14

As shown in Table 3 above, a SIgA response against CFA/I, CS3 and Shigella LPS was detected in tears of guinea pigs after orogastric (o.g.) or intranasal (i.n.) immunization (Noriega et al, (1996) supra). The above observations provide the rationale in the present invention for a strategy to prepare a broad-spectrum live oral vaccine against both ETEC and Shigella. This is, in the present invention, a multivalent hybrid vaccine consists of a series of attenuated Shigella serotypes expressing the major fimbrial colonization factor antigens of ETEC (CFA/I and CS1-6), and the B subunit of heat-labile enterotoxin (LTB) of ETEC (or a mutant thereof).

B. Attenuated Shigella Strains as DNA-mediated Vaccines

Direct DNA immunization is one of the cutting-edge methods in experimental vaccinology used today. Usually, this method consists of direct immunization with genes encoding antigens from the pathogen of interest inserted into a plasmid that may replicate and express such antigen, under the control of a viral or eukaryotic promoter, in the cells of the immunized animal (or human). Cell-mediated and/or humoral immune responses have been achieved with this method of immunization against antigens belonging to a diversity of pathogens, such as: influenza (Justewicz et al, *J. Virol.*, 69:7712–7717 (1995); and Fynan et al, *Int. J. Immunopharmacol.*, 17:79–83 (1995)), lymphocytic choriomeningitis virus (Zarozinski et al, *J. Immunol.*, 154:4010–4017 (1995)), human immunodeficiency virus (Shiver et al, *Ann. NY. Acad. Sci.*, 772:198–208 (1995)), hepatitis B virus (Davis et al, *Vaccine*, 12:1503–1509 (1994) ), hepatitis C virus (Lagging et al, *J. Virol.*, 69:5859–5863 (1995)), rabies virus (Xiang et al, *Virology*, 209:569–579 (1995)), *Schistosoma* (Yang et al, *Biochem. Biophys. Res. Commun.*, 212:1029–1039 (1995)), *Plasmodium* (Sedegah et al, *Proc. Natl. Acad. Sci.*, 91:9866–9870 (1994)) and mycoplasma (Barry et al, *Nature*, 377:632–635 (1995)); or even cancerous cells, such as: B cell lymphoma (Stevenson et al, *Ann. NY Acad. Sci.*, 772:212–226 (1995)) or colon carcinoma (Conry et al, *Cancer Gene Ther.*, 2:33–38 (1995) ). The usual channels of delivery for these DNA-mediated vaccines have been by intramuscular injection (Lagging et al, supra; and Yang et al, supra), or by the use of a gene-gun device (Fynan, et al, supra; and Zarozinski et al, supra).

Recently, it has been demonstrated that an attenuated strain of Shigella can be used as a delivery system of genes which are expressed by the eukaryotic host (Sizemore et al, *Science*, 270:299–302 (1995)). Shigella spp. are invasive organisms that abandon the phagolysosome vacuole at a point following invasion. An attenuated Shigella strain may die shortly thereafter, releasing its content in the cytoplasm of the host cell. Thus, released plasmids that can replicate in the eukaryotic cell may then start expressing the selected antigens which will be processed and presented to the immune system, as in the case when these plasmids are introduced by injection or "bombardment" with a gene-gun.

VI. Shigella with Mutations in the Purine Metabolic Pathway purA and purB mutations in Salmonella (interrupting the de novo biosynthesis of adenine nucleotides) (see FIG. 1) are so highly attenuating (McFarland et al, *Microb. Pathogen.*, 3:129–141 (1987)), that these strains are non-protective in animals (O'Callagham et al, *Infect. Immun.*, 56:419–423 (1988)), and poorly immunogenic in humans (Levine et al, *J. Clin. Invest.*, 79:888–902 (1987)). In contrast, mutations in several of the genes involved in the common purine pathway (i.e., purF, purG, purC, purHD) that interrupt the biosynthesis of both purine nucleotides (see FIG. 1), or in guaB or guaA, thereby interrupting the biosynthesis of guanine nucleotides (see FIG. 1), are far less attenuating (McFarland et al, supra); indeed, such strains induced death in mice in doses as low as $10^2$ cfu (McFarland et al, supra). It has been reported that $pur^-$ auxotrophs of *S. flexneri* 2a and *S. sonnei* (derived by non-specific mutagenesis) are not significantly attenuated (Linde et al, *Vaccine*, 8:25–29 (1990)); and guinea pigs inoculated in their conjunctival sac with these strains developed full-blown purulent keratoconjunctivitis (positive Sereny test (Sereny, *Acta Microbiol. Acad. Sci. Hung.*, 4:367–376 (1957); and Linde et al, supra).

The observations reviewed above suggest that:

11

(i) mutations affecting enzymes of the common purine pathway are mildly attenuating (McFarland et al, supra); and (ii) mutations distal to the common pathway and affecting the synthesis of adenine nucleotides are over-attenuating (i.e., purA, purB) (McFarland et al, supra; O'Callagham et al, supra; and Levine et al, (1987) supra), but distal mutations affecting the guanine nucleotide synthesis are only minimally attenuating (McFarland et al, supra).

It was unexpectedly discovered in the present invention that a gua⁻ auxotrophy in Shigella provided a high degree of attenuation. This attenuation is believed to be due to reduced invasion capability, and a decreased intracellular replication rate of the guaB-A Shigella mutants of the present invention.

This finding was unexpected since Salmonella harboring mutations affecting guanine nucleotide synthesis are only minimally attenuating (McFarland et al, supra). Further, despite the high degree of attenuation, it was unexpectedly discovered in the present invention that the guaB-A Shigella mutants of the present invention are highly immunogenic and protective. This finding was unexpected since Salmonella harboring mutations in purA or purB (genes involved in the last steps of the synthesis of adenine nucleotides in the de novo purine pathway), though highly attenuated, are poorly immunogenic and non-protective (O'Callagham et al, supra; and Levine et al, (1987) supra); and pur⁻ auxotrophs of Shigella are not significantly attenuated (Linde et al, supra).

SUMMARY OF THE INVENTION

An object of the present invention is to provide Shigella strains of diverse serotypes attenuated by mutations in the de novo guanine metabolic pathway.

Another object of the present invention is to provide an oral vaccine against shigellosis.

Yet another object of the present invention is to provide Shigella strains which are useful as live vectors of foreign genes cloned from other pathogens, and that upon expression and appropriate immunization, will raise protective immune responses against the pathogens from which the foreign antigens were derived.

Another object of this invention is to provide Shigella strains which are useful as carriers of genes not expressed in Shigella, but that are cloned from other pathogens that are expressed in the eukaryotic cell of the host (animal model or human), and that raise protective immune responses against the pathogens from which the foreign antigens were derived.

Still another object of this invention is to provide a method to achieve a deletion mutation in the guaB and guaA genes of Shigella.

These and other objects of the present invention, which will be apparent from the detailed description of the invention provided below, have been met in one embodiment by a Shigella mutant which is incapable of forming de novo guanine nucleotides, wherein said mutant contains a mutation in the gua gene.

BRIEF DESCRIPTION OF THE DRAWINGS

In FIG. 1, interrupted arrows illustrate pathways in which the individual steps are not represented. Enzymes are represented by their genes. Superscript letters represent selected strains with a mutation of the gene involved in that reaction. The strains represented are: a: purF1741::Tn10 *S. dublin* SL5437 (McFarland et al, supra); b: purG876::Tn10 *S. dublin* SL5436 (McFarland et al, supra); c: purC882::Tn10 *S. dublin* SL5435 (McFarland et al, supra); d: purH887::Tn10 *S. dublin* SL2975 (McFarland et al, supra); e: ΔguaB-A *S. flexneri* 2a CVD1204 and ΔguaB-A, ΔvirG CVD1205 (the present invention)); f: aroD25::Tn10 *S. flexneri* Y SFL114 (Lindberg et al, (1990) supra), SFL124 (Li et al, supra), *S. flexneri* 2a 1070 (Karnell et al, (1995) supra); g: ΔaroC, ΔaroD *S. typhi* CVD908 (Hone et al, supra); h: hisG46 DEL407, aroA554::Tn10 *S. typhimurium* SL3261 (Hoiseth et al, supra); i: ΔaroA *S. flexneri* 2a CVD1201 and ΔaroA, ΔvirG CVD1203 (Noriega et al, 1994) supra); and j: ΔaroA, ΔvirG, ΔpurA *S. typhi* 541Ty (Levine et al, (1987) supra). In FIG. 1, the abbreviations are defined as follows: PRPP: 5-phosphoribosyl-α-1-pyrophosphate; PRA: 5-phosphoribosylamine; GAR: 5'-phosphoribosyl-1-glycinamide; FGAR: 5'-phosphoribosyl-N-formylglycinamide; FGAM: 5'-phosphoribosyl-N-formylglycinamidine; AIR: 5'-phosphoribosyl-5-aminoimidazole; CAIR: 5'-phosphoribosyl-5-aminoimidazole-4-carboxylic acid; SAICAR: 5'-phosphoribosyl-4-(N-succinocarboxamide)-5-aminoimidazole; AICAR: 5'-phosphoribosyl-4-carboxamide-5-aminoimidazole; FAICAR: 51-phosphoribosyl-4-carboxamide-5-formamidoimidazole; IMP: inosinic acid; Hx: hypoxanthine; G: guanine; and A: adenine.

FIGS. 2A-2G show the DNA sequence encoding the guaA and guaB genes of *Escherichia coli* (SEQ ID NO:1) (GenBank accession No. M10101 M10102) (Thomas et al, *Gene*, 36:45-53 (1985); Tiedeman et al, *J. Biol. Chem.*, 260:8676-8679 (1985); and Tiedeman et al, *Nucleic Acids Res.*, 13:1303-1316 (1985)), which is considered to be highly homologous with the guaA and guaB of Shigella spp., as well as some restriction endonuclease sites useful in creating the deletion mutants of the present invention.

DETAILED DESCRIPTION OF THE INVENTION

The present invention provides attenuated Shigella for use, inter alia, as oral vaccines against shigellosis, as live vector and DNA-mediated vaccines expressing foreign antigens. As used herein, a "foreign antigen" means an antigen foreign to Shigella.

Figure 1:
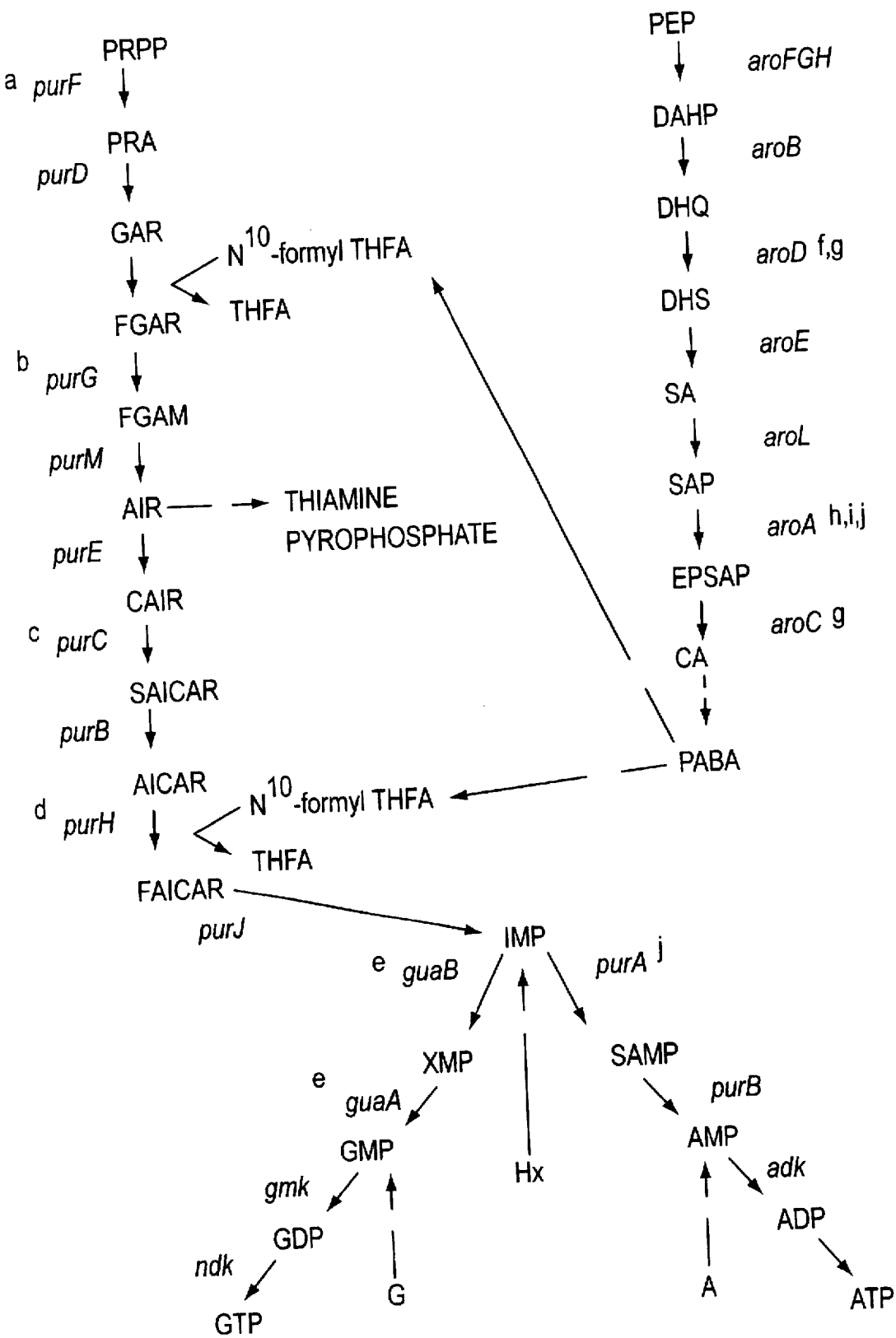
FIG. 1 shows the purine de novo biosynthesis pathway and contribution of the aromatic metabolic pathway.
Figure 3:
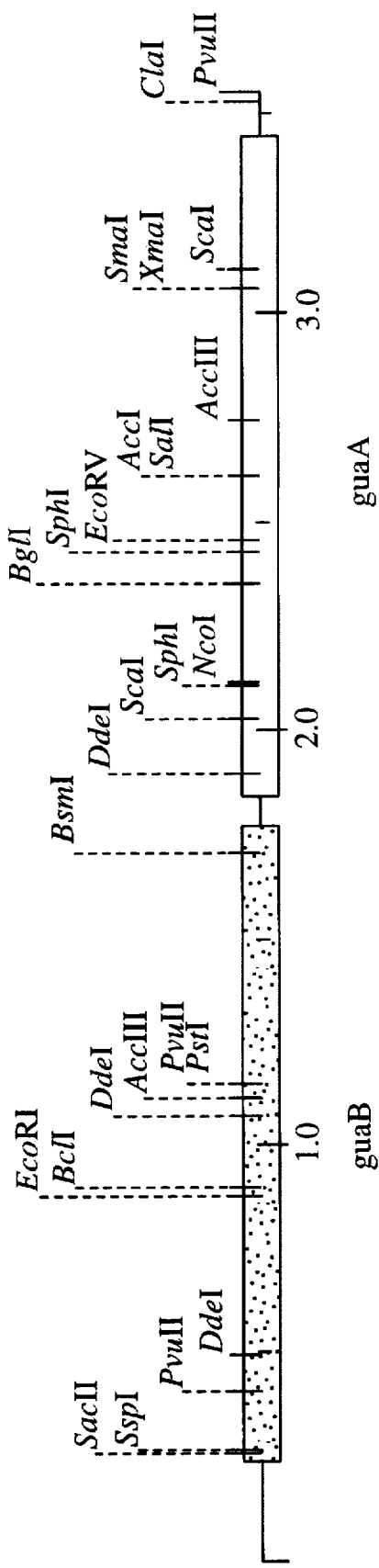
FIG. 3 schematically shows the orientation of the guaB-A operon, as well as the location of some restriction endonuclease sites useful in creating the deletion mutants of the present invention.

In the present invention, the chromosomal genome of Shigella is modified by removing or otherwise modifying the guaB-A operon, and thus blocking the de novo biosynthesis of guanine nucleotides. Preferably, a defined, in frame, non-polar mutation in the guaB-A operon inactivates the purine metabolic pathway enzymes IMP dehydrogenase (encoded by guaB) and GMP synthetase (encoded by guaA). As consequence of this mutation, Shigella are unable to de novo synthesize GMP, and consequently GDP and GTP nucleotides (see FIG. 1), which severely limits its grow in mammalian tissues. In vitro, the guaB-A mutants of the present invention are unable to grow in minimal medium unless supplemented with guanine. In tissue cultures, the guaB-A Shigella mutants of the present invention were found to show a significant reduction in their capability for invasion. In vivo, these mutants are dramatically attenuated, but nonetheless confer a striking protective immune response. guaB-A mutants may scavenge guanine nucleotides from the tissues of the mammalian host. However, their assimilation into Shigella requires prior dephosphorylation to nucleosides by periplasmic nucleotidases to be incorporated as nucleotide precursors into the guanine salvage pathway. Therefore, as nucleotides are readily available in the intracellular environment of the mammalian host, the attenuation due to the de novo synthesis of guanine nucleotides is due either to the inefficiency of the salvage pathway or to reasons that are obscure to today's knowledge.

The particular Shigella spp. employed as a starting material in the present invention is not critical thereto. There are 47 serotypes of Shigella spp. identified to-date as human pathogens belonging to the S. flexneri, S. dysenteriae, S. boydii and S. sonnei groups. Strains belonging to any of these serotypes can be attenuated with the techniques described herein, and such attenuated strains are included within the scope of the present invention.

In this respect, the construction of 3 examples of Shigella vaccines of different serotypes is specifically described herein. These vaccines were constructed with strains from the highly prevalent serotypes S. flexneri 2a, S. sonnei, and S. dysenteriae type 1.

S. flexneri 2a is a well-known virulent Shigella serotype available from a variety of sources, such as the CVD, the Centers for Disease Control (CDC), the Walter Reed Army Institute of Research, the Uniformed Services University of the Health Sciences, and the Institut Pasteur. The particular parent strain of S. flexneri 2a employed in the present invention is not critical thereto. Examples of such S. flexneri 2a strains include M4243, M4243avir, a non-invasive plasmidless strain derived from 2457T (Fasano et al, J. Clin. Invest., 95:2853–2861 (1995)), S. flexneri 2a Chile 747, S. flexneri 2a Chile 3480 (Ferreccio et al, supra); strain 2457T (Kotloff et al, (1992) supra; BS103 (Andrews et al, Infect. Immun., 59:1997–2005 (1991)); and ΔaroA S. flexneri 2a strain CVD 1201, derived from strain 2457T (Noriega et al, (1994) supra). S. flexneri 2a strain 2457T, originally isolated in Japan, is known to cause disease in volunteers (DuPont et al, J. Infect. Dis., 119:296–299 (1969)). The preferred S. flexneri 2a strain employed in the present invention is Shigella flexneri 2a strain 2457T.

S. flexneri 2a strain 2457T can be obtained from a variety of sources, e.g., Dr. Thomas L. Hale of the Walter Reed Army Institute of Research, Washington, D.C. Strain BS103 can be obtained from Dr. Anthony Maurelli of the Uniformed Services University of the Health Sciences, Bethesda, Md.

S. dysenteriae type 1 serotype is also a well-known virulent Shigella serotype readily available from a variety of sources. The particular parent strain of S. dysenteriae employed in the present invention is not critical thereto. Examples of such S. dysenteriae strains include: strain 7/87, which can be obtained from Dr. Philippe Sansonetti of the Institut Pasteur (Fontaine, et al, Res. Microbiol., 141:907–912 (1990)); and strain 1617, which can be obtained from the CVD strains collection (Levine et al, (1973) supra).

S. sonnei is also a well-known virulent Shigella serotype available from a variety of sources, such as the Walter Reed Army Institute (WRAIR), the Uniformed Services University of the Health Sciences, the CDC, the Institute Pasteur and the Swiss Serum and Vaccine Institute (SSVI). Examples of such S. sonnei strains include: strain G53, which can be obtained from the CVD strains collection (Herrington et al, supra), and from Dr. Thomas L. Hale at WRAIR; and strain 482–79, which can be obtained from Dr. Favre at SSVI (Favre et al, Infect. Immun., 64:576–584 (1996)).

The guaA gene, which encodes GMP synthetase, is 1575 bp in size (see FIGS. 2A–2G). Thus, the size of an intracistronic inactivating deletion in the guaA mutant may range from 1 to 1575 bp, preferably, from 100 to 1575 bp if the deletion is in-frame. Deletions can also be made that extend beyond the guaA gene, i.e., extracistronic deletions downstream of the guaA may affect the transcription of this gene, and therefore inactivate it. However, the latter is not preferable.

The guaB gene, which encodes IMP dehydrogenase, is 1533 bp in size (see FIGS. 2A–2G). Thus, the size of an intracistronic deletion in the guaB mutant may range from 1 bp to 1533 bp, preferably, from 100 to 1533 bp if the deletion is in-frame. Deletions can also be made that extend beyond the guaB gene, i.e., extracistronic deletions downstream of the guaB may affect the transcription of both genes (guaB and guaA), and therefore inactivate it. However, the latter is not preferable.

Deletions can be made in the guaA gene using 2 convenient restriction sites located in the guaA gene; examples of these are ScaI or AccI and EcoRV or SalI or SmaI or SphI or XmaI (FIGS. 2A–2G and FIG. 3), or by site-directed mutagenesis with oligonucleotides (Sambrook et al, In: Molecular Cloning, A Laboratory Manual, Eds., Cold Spring Harbor Publications (1989)).

Deletions can be made in the guaB gene using two convenient restriction sites located in the guaB gene; examples of these are BclI and BsmI or EcoRI or PvuII or SacII or SspI or XhoII (FIGS. 2A–2G and FIG. 3), or by site-directed mutagenesis with oligonucleotides (Sambrook et al, supra).

In addition, any combination of restriction sites located simultaneously in the guaB and guaA genes can be used to obtain the deletion mutants of the present invention; examples of these are AccIII, AflIII, AhaII, AlwI, AlwNI, AsuI, BanI, BcnI, Bsp1286, BspMII, and DdeI (FIGS. 2A–2G).

Inactivation of the guaA gene and/or guaB gene can also be carried out by an insertion of foreign DNA using any of the above-mentioned restriction sites, or by site-directed mutagenesis with oligonucleotides (Sambrook et al, supra) so as to interrupt the correct transcription of guaB and/or guaA. The typical size of an insertion that can inactivate the guaA gene and guaB gene is from 1 base pair to 100 kbp, although insertions smaller than 100 kbp are preferable. The insertion can be made anywhere inside the guaA gene or guaB gene coding region or between the coding region and the promoter.

Other methods for the guaA gene and/or guaB gene inactivation include the transfer into Shigella spp. of deletions or insertions made in E. coli guaA or guaB genes, transposon-generated deletions, and imprecise excision of DNA insertions. The latter two methods are more likely to make deletions that extend beyond the guaA or guaA gene, and therefore are not preferable.

The gua mutants of the present invention are useful for the development of a non-reactogenic Shigella candidate live oral vaccine.

Shigella spp. vaccine candidates can be constructed which, e.g., in addition to containing other attenuating mutations, fail to express the guaA and/or guaB gene products. This can be accomplished by deleting the portion of the gua genes in a Shigella spp. strain in which deletion mutations have been introduced in at least one aro gene (aroA, aroC, or aroD) of the Shigella chromosome, rendering the strain auxotrophic for PABA, a substrate that cannot be scavenged in the mammalian cell, such as *Shigella flexneri* 2a strain CVD1203 (ATCC No. 55556).

In addition, the mutants of the present invention will preferably have an independently attenuating, deletion mutation in the virG gene, which is found on the 140 MD invasiveness plasmid of Shigella spp. This plasmid gene, also known as icsa (Sansonetti et al, (1989) supra), is involved with the intracellular and intercellular spread of Shigella. This mutation is also present in CVD1203.

Moreover, it is desirable that the mutants of the present invention have a deletion in either the gene encoding ShET1 and/or the gene encoding ShET2 (set1 and sen, respectively) (U.S. Pat. No. 5,468,639; and allowed U.S. patent application Ser. No. 08/351,147, filed Nov. 30, 1994; which are incorporated by reference herein in their entirety). The particular size of the deletion in either the gene encoding ShET1 and/or the gene encoding ShET2 is not critical to the present invention.

In a preferred embodiment, the above-described objects of the present invention have been met by an guaA, guaB double mutant of Shigella spp.

In yet another embodiment, the above-described objects of the present invention have been met by a vaccine against Shigellosis comprising:

(A) a pharmaceutically effective amount of a Shigella mutant which is incapable of forming de novo guanine nucleotides, wherein said mutant contains a mutation in the guaB-A operon; and (B) a pharmaceutically acceptable carrier or diluent.

In still another embodiment, the above-described object of the present invention has been met by a live vector vaccine comprising:

(A) a pharmaceutically effective amount of a Shigella mutant which is incapable of forming de novo guanine nucleotides, wherein said mutant contains a mutation in the guaB-A operon, and wherein said mutant encodes and expresses a foreign antigen; and (B) a pharmaceutically acceptable carrier or diluent.

The particular foreign antigen employed in the Shigella live vector is not critical to the present invention. The attenuated Shigella strain(s) of the present invention may be used as a live vector(s) for immunization against enteric pathogens (pathogen defined as bacterial, viral, protozoal, etc.), sexually transmitted disease pathogens or pathogens with a mucosal entry that lead to grave systemic manifestations of disease.

Examples of antigens from enteric pathogens that may be expressed in the Shigella live vectors of the present invention include: major fimbrial colonization factor antigens of ETEC (CFA/I, CS1-6) plus heat-labile enterotoxin subunit B (LTB), or mutant heat-labile enterotoxin ("holotoxoid") (Pizza et al, *Mol. Microbiol.*, 14:51–60 (1994)) so as to prevent ETEC-associated diarrhea; subunit B of Shiga toxin (Strockbine et al, *J. Bacteriol.*, 170:1116–1122 (1988)) and Shiga-like toxin II (SLTII) (Jackson et al, *FEMS Microbiol. Lett.*, 44:109–114 (1987)) so as to prevent complications (such as hemolytic uremic syndrome) associated with enterohemorragic *E. coli* (EHEC); and toxin A (Sauerborn et al, *Nucleic Acids Res.*, 18:1629–1630 (1990)) and toxin B (Barroso et al, *Nucleic Acids Res.*, 18:4004 (1990)) of *Clostridium difficile* so as to prevent pseudomembranous colitis.

Examples of antigens from sexually transmitted diseases pathogens that may be expressed in the Shigella live vectors of the present invention include: Herpes simplex virus glycoprotein D (Watson et al, *Science*, 218:381–384 (1982)) so as to prevent genital, mucosal (oral, anal conjunctival) and systemic infections with these organisms; protein I (Carbonetti et al, *Proc. Natl. Acad. Sci. U.S.A.*, 84:9084–9088 (1987)), pilin (GenBank Accession No. Z49122), H.8 antigen (Lip) (Baehr et al, *Mol. Microbiol.*, 3:49–55 (1989)) and the major iron-regulated protein (MIRP) (Berish et al, *J. Exp. Med.*, 171:1535–1546 (1990)) of *Neisseria gonorrhea* so as to prevent gonorrhea.

Examples of antigens from pathogens with a mucosal entry that have systemic manifestations of disease that may be expressed in the Shigella live vectors of the present invention include: *Neisseria meningitidis* group B outer membrane proteins (OMPs), such as transferrin binding protein 2 (tbp2) (Legrain et al, *Gene*, 130:73–80 (1993)), Opc (class 5 protein) (Olyhoek et al, *Microb. Pathog.*, 11:249–257 (1991)) and PorA (Saunders et al, *Gene*, 137:153–162 (1993)) so as to prevent Group B *meningococcus meningitis* and sepsis.

In addition, other antigens used to prevent non-infectious processes may be delivered by attenuated Shigella live vectors of the present invention, such as: human carcinoembryonic antigen (Beauchemin et al, *Mol. Cell. Biol.*, 7:3221–3230 (1987)) to prevent colon cancer; or human testis lactate dehydrogenase gene (Cooker et al, *Biol. Reprod.*, 6:1309–1319 (1993)) to prevent pregnancy.

In still another embodiment, the above-described objects of the present invention has been met by a DNA-mediated vaccine comprising:

(A) a pharmaceutically effective amount of a Shigella mutant which is incapable of forming de novo guanine nucleotides, wherein said mutant contains a mutation in the guaB-A operon; wherein said mutant contains a plasmid which encodes and expresses in a eukaryotic cell, a foreign antigen; and (B) a pharmaceutically acceptable carrier or diluent.

Details as to the construction and use of DNA-mediated vaccines can be found in U.S. patent application Ser. No. 08/433,790, filed May 3, 1995, which is incorporated by reference herein in its entirety.

The particular foreign antigen employed in the DNA-mediated vaccine is not critical to the present invention. Examples of such antigens include those from a diversity of pathogens, such as influenza (Justewicz et al, *J. Virol.*, 69:7712–7717 (1995); and Fynan et al, *Int. J. Immunopharmacol.*, 17:79–83 (1995)), lymphocytic choriomeningitis virus (Zarozinski et al, *J. Immunol.*, 154:4010–4017 (1995)), human immunodeficiency virus (Shiver et al, *Ann. NY. Acad. Sci.*, 772:198–208 (1995)), hepatitis B virus (Davis et al, *Vaccine*, 12:1503–1509 (1994)), hepatitis C virus (Lagging et al, *J. Virol.*, 69:5859–5863 (1995)), rabies virus (Xiang et al, *Virology*, 209:569–579 (1995)), *Schistosoma* (Yang et al, *Biochem. Biophys. Res. Commun.*, 212:1029–1039 (1995)), *Plasmodium* (Sedegah et al, *Proc. Natl. Acad. Sci.*, 91:9866–9870 (1994)); and mycoplasma (Barry et al, *Nature*, 377:632–635 (1995)).

The decision whether to express the foreign antigen in Shigella (using a prokaryotic promoter in a live vector vaccine) or in the cells invaded by Shigella (using a eukaryotic promoter in a DNA-mediated vaccine) may be based upon which vaccine construction for that particular antigen gives the best immune response in animal studies or in clinical trials, and/or, if the glycosylation of an antigen is essential for its protective immunogenicity, and/or, if the correct tertiary conformation of an antigen is achieved better with one form of expression than the other.

In the vaccines of the present invention, the pharmaceutically effective amount of the mutants of the present invention to be administered will vary depending on the age, weight and sex of the subject. Generally, the dosage employed will be about $10^5$ cfu to $10^{10}$ cfu, preferably about $10^6$ cfu to $10^9$ cfu.

The particular pharmaceutically acceptable carrier or diluent employed is not critical to the present invention, and are conventional in the art. Examples of diluents include: buffer for buffering against gastric acid in the stomach, such as citrate buffer (pH 7.0) containing sucrose, bicarbonate buffer (pH 7.0) alone (Levine et al, (1987) supra; and Black et al, supra), or bicarbonate buffer (pH 7.0) containing ascorbic acid, lactose, and optionally aspartame (Levine et al, Lancet, II:467–470 (1988)). Examples of carriers include: proteins, e.g., as found in skim milk; sugars; e.g. sucrose; or polyvinylpyrrolidone.

The mutants of the present invention can be stored at –70° C. while suspended in Luria broth (DIFCO) containing 30%–50% (v/v) glycerol.

The following examples are provided for illustrative purposes only, and are in no way intended to limit the scope of the present invention.

EXAMPLE 1

Construction of ΔguaB-A *S. flexneri* 2a Strains

A. Construction of the ΔguaB-A Deletion Cassette pFM726A

Figure 4:
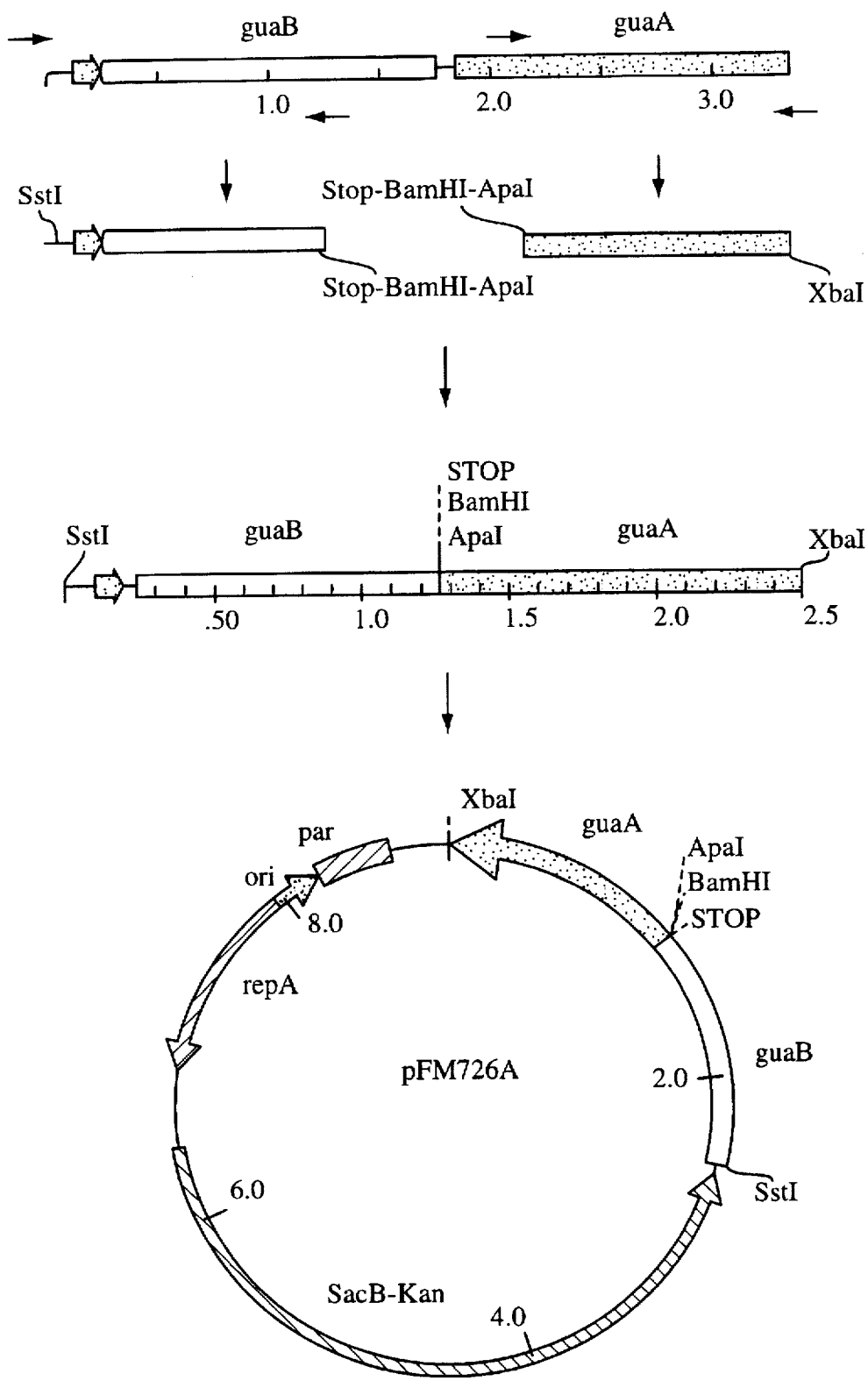
FIG. 4 is a schematic illustration of the construction of the ΔguaB-A deletion cassette, pFM726A.
Figure 5:
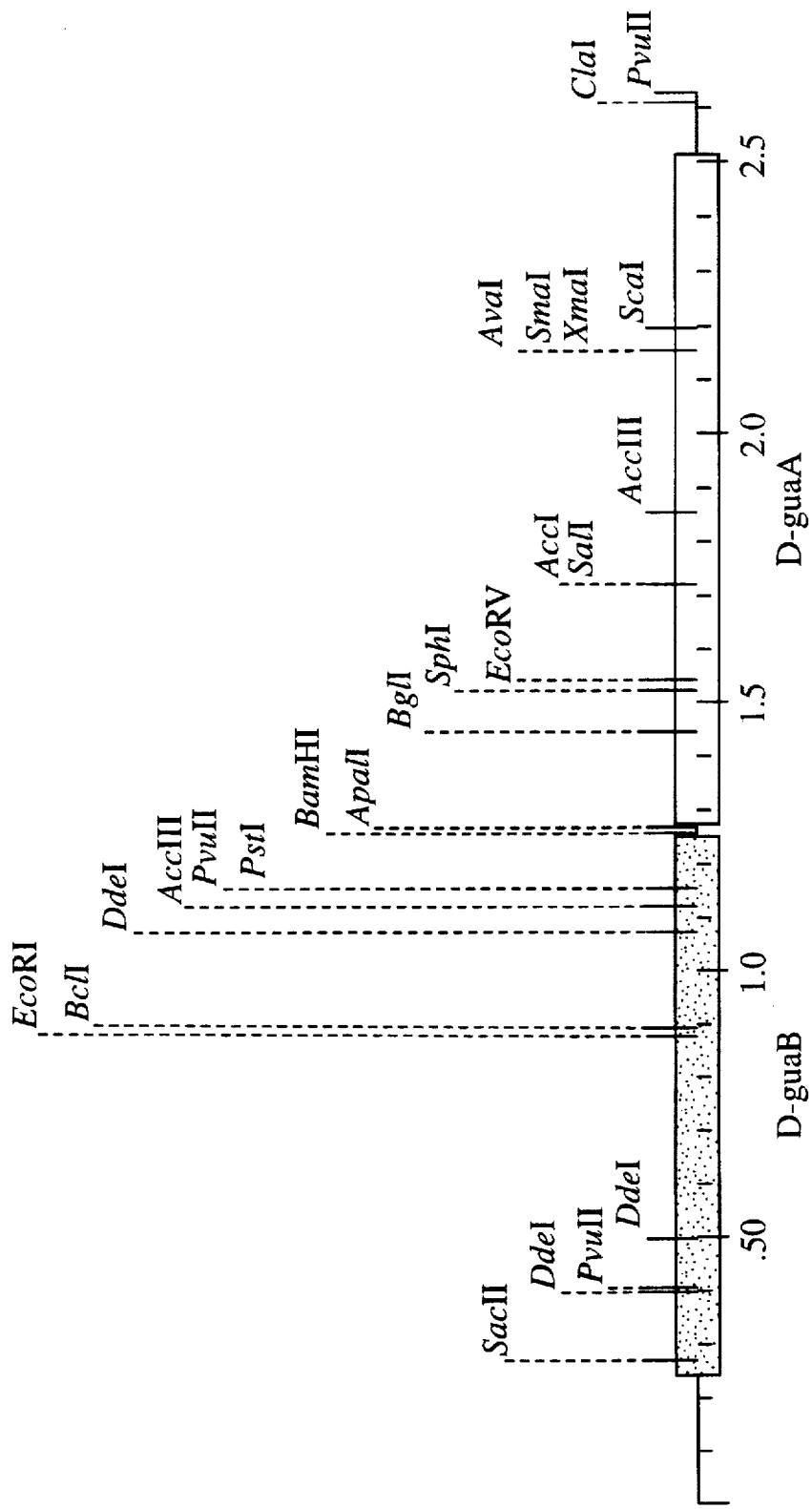
FIG. 5 is a schematic representation of the ΔguaB-A allele.

DNA segments that include the 5' terminus of the guaB gene, and the 3' terminus of the guaA gene were amplified by PCR using *S. flexneri* 2a genomic DNA as template, and then fused in a second PCR reaction, thereby giving rise to the ΔguaB-A allele (FIG. 4 and FIG. 5). The methods used in the construction of the ΔguaB-A allele were analogous to those described in the construction of the ΔaroA allele in the construction of strain CVD 1203 (Noriega et al, (1994) supra).

In the first PCR reaction (FIG. 4) the primers used to amplify the 5' terminus of the ΔguaB-A allele were:

5'-CGAGCTCGCGAGCTCGGTAAAGTACCAGTGA CCGGAAGCTGGTTGCGT-3' (SEQ ID NO:2); and

5'-GGGCCCGGGGGATCCTCAACCGACGCCAGTC ACGATACGAGTTGTACAGAT-3' (SEQ ID NO:3); and the primers used to amplify the 3' terminus of the ΔguaB-A allele were:

5'-TGAGGATCCCCCGGGCCCGGCTACGCGCAGG TTGAAGTCGTAAACGACAGC-3' (SEQ ID NO:4); and

5'-GCTCTAGAGCTCTAGAGCTCATTCCCACTCAA TGGTAGCTGGCGGCTT-3' (SEQ ID NO:5).

Within the internal primers (SEQ ID NOS:3 and 4) were introduced an in-frame stop signal codon (TGA and TCA) upstream of two unique restriction sites (ApaI and BamHI) (underlined) that were added for the introduction of foreign genes into the chromosomal ΔguaB-A allele. The stop signal avoids translational fusions of the ΔguaB with ΔguaA products, or of the ΔguaB product with the products of foreign inserted genes in the middle of the ΔguaB-A allele. In addition, these internal primers introduced sequences that served as the homologous region (in bold) with which the 5' and 3' PCR products were fused in a second PCR reaction (thus forming the ΔguaB-A allele) (FIG. 4 and FIG. 5). In the second PCR reaction, the 5' and 3' segments were fused and the resultant fusion was amplified in the same reaction. In this reaction, the given homologous region (ApaI-BamHI) annealed, effectively fusing the 5' and 3' segments which at that time may have acted as their own primers and/or templates for the Taq polymerase, depending upon which strands of DNA were annealed. To facilitate this fusion, a PCR-program was designed in which the first 15 cycles had an annealing temperature slope (1° C./8 sec from 40° C. to 50° C. +50° C. for 2 min), followed by 15 cycles with an annealing temperature of 55° C. in which the new ΔguaB-A allele was amplified. Thus, there were 900 base pairs of the guaB-A operon that were not amplified, giving rise to ΔguaB-A (FIG. 5).

The extreme primers (SEQ ID NOS:2 and 5) were designed to introduce unique restriction sites (SstI and XbaI) (underlined) that were used to clone the ΔguaB-A allele into unique restriction sites in the temperature-sensitive, pSC101-based (Blomfield et al, *Mol. Microbiol.*, 5:1447–1457 (1991)) suicide plasmid pFM307A, giving rise to pFM726A (FIG. 4). Plasmid FM307A (6.3 Kbp) was constructed by substituting a 4.3 Kbp NaeI-NaeI fragment, containing the cam gene (chloramphenicol resistance) in pIB307 (Blomfield et al (1991), supra) with a 3.8 Kbp BamHI-BamHI fragment (blunt-ended by Klenow polymerase) containing the SacB-Kan cassette (providing resistance to kanamycin and sucrose counter-selection) from pIB279 (Blomfield et al (1991), supra) (FIG. 4).

B. Suicide Deletion Cassette-Driven Deletion Mutations

Deletion cassette pFM726A was used to introduce the ΔguaB-A deletion mutation into wild-type *S. flexneri* 2a strain 2457T by homologous recombination, as described by Blomfield et al, supra; and Noriega et al, (1994) supra.

C. Screening of Mutants by DNA Probes and PCR

Candidate bacterial clones were grown at 37° C. overnight in a grid pattern on Luria agar plates or in Shigella minimum medium (Noriega et al, (1994) supra). The colonies were then transferred to No. 541 filter paper (Whatman, Maidstone, England), and blotted as described by Gicquelais et al, *J. Clin. Microbiol.*, 28:2485–2490 (1990), and probed using a $\gamma P^{32}$-labeled 40 bp oligonucleotide:

5'-GGGCGGCCTGCGCTCCTGTATGGGTCTGACCG GCTGTGGT-3' (SEQ ID NO:6), corresponding to a deleted portion of the guaB-A wild-type allele (negative probe). Clones grown in Shigella minimum medium failed to hybridize with the $\gamma P^{32}$-labeled 40 bp oligonucleotide probe were selected. The ΔguaB-A *S. flexneri* 2a clones were not able to grow in Shigella minimal medium unless supplemented with 10 mg of guanine/l.

Thereafter, the ΔguaB-A allele was amplified from the probe-negative clones by PCR using the same extreme primers used in the construction of the ΔguaB-A allele (FIG. 4), yielding a 2.3 Kbp product vs. a 3.2 Kbp product for the wild-type guaB-A allele.

One ΔguaB-A *S. flexneri* 2a clone was arbitrarily selected and named CVD 1204, after confirming that the Shigella invasion plasmid was still present.

A specific, in-frame, deletion mutation in the virG gene was also accomplished using a plasmid suicide vector deletion cassette (pΔvirG) containing ΔvirG as described by Noriega et al, (1994), supra. The deletion mutation corresponds to 900 base pairs representing amino acids 341-640 of the 120 kDa VirG protein. The specific engineered site for this deletion in the protein represents a highly hydrophobic, poorly antigenic portion of the molecule according to the Jameson/Wolf antigenic index (IBI Pustell Sequence Analysis Programs).

The construction of the ΔvirG allele followed the analogous steps as used in the construction of the guaB-A mutation. That is, the 5' segment was amplified with the following primers:

5'-GGGGAATTCCAAATTCACAAATTTTTTTGT-3' (SEQ ID NO:7), and

5'-TCCATGCCATTCATGGAGTATTAATGAATT-3' (SEQ ID NO:8), while the 3' segment was amplified with the following primers:

5'-CTCCATGAATGGCATGGAAAGGCGGAATA-3' (SEQ ID NO:9) and

5'-CGGGTCGACTCAGAAGGTATATTTCACACCCAA-3' (SEQ ID NO:10).

As for the construction of AguaB-A, the two segments were fused in a second PCR reaction. In this case, the ΔvirG allele was cloned into the EcoRI and SalI sites of the suicide plasmid pKTN701 (Hone et al, Vaccine, 9:810–816 (1991)), using the corresponding sites added to this gene with the extreme primers (SEQ ID NOS: 7 and 10) (underlined), giving rise to pShvirG. Plasmid pShvirG was incorporated as a cointegrate into the virG locus of the invasiveness plasmid of S. flexneri 2a strain CVD 1204, following conjugation with E. coli strain Sm10 λpir as the donor (first homologous recombination with wild-type gene). These cointegrate colonies were detected by selecting isolates that were resistant to chloramphenicol. After a second homologous recombination, the suicide vector was cured, and in a proportion of those colonies the ΔvirG replaced the wild-type gene.

To confirm the deletion mutation on the invasion plasmid's virG allele, two probes were generated, a $\gamma P^{32}$-labeled 40 bp oligonucleotide:

5'-GGGGACAGTTGAAGCTATGACACGTACCGCTG GTGTTATT-3' (SEQ ID NO:11), corresponding to a deleted portion of the wild-type gene (negative probe), and a PCR-generated (using the same extreme primers described above), $\alpha P^{32}$-labeled ΔvirG allele (positive probe). This second probe was introduced to rule out (at the time of screening for mutants) that the clones that did not hybridize with the negative probe had lost the virulence plasmid during the process of curing the suicide plasmid. The deletion mutation in virG was confirmed genotypically by PCR amplification of the deleted allele using the extreme primers described above (yielding a 2.5 Kbp for ΔvirG vs. 3.5 Kbp for wild-type virG).

One AguaB-A, ΔvirG S. flexneri 2a clone was arbitrarily selected and named CVD 1205. CVD 1205 has been deposited at the American Type Culture Collection on Apr. 9, 1996, under ATCC No. 55757.

Phenotypically, the deletion ΔvirG mutation in CVD 1205 was confirmed by assaying for the expression of a truncated VirG protein visualized in Western immunoblotting.

More specifically, whole cell proteins were prepared by 10 min boiling of overnight cultures resuspended in lysing buffer comprising 0.125% (w/v) Tris-HCl (pH 6.8), 4.0% (w/v) SDS, 20% (v/v) glycerol, 10% (v/v) 2-mercaptoethanol, and 0.1% (w/v) bromophenol blue (SIGMA). VirG protein was resolved by gel electrophoresis in 10% (w/v) SDS-PAGE, and transferred to nitrocellulose paper. Immunoblot identification of virG was accomplished with a rabbit antiserum generated against a VirG peptide $Leu_{55}$-Thr73 (obtained from Dr. Edwin V. Oaks, Walter Reed Army Institute of Research, Washington, D.C.), and developed with an alkaline phosphatase-conjugated goat anti-rabbit IgG (SIGMA).

The ΔvirG deletion mutants showed a predicted 90 kDa band vs. 120 Kd band for wild-type VirG protein.

EXAMPLE 2

Invasion and Intracellular Growth in Tissue Cultures

HeLa cell gentamicin protection assays were performed to assay the invasion and intracellular growth of, inter alia, CVD1204, as essentially as described by Lindberg et al, (1990) supra; Oaks et al, Infect. Immun., 48:124–129 (1985); and Noriega et al, (1994) supra.

More specifically, semi-confluent HeLa cell monolayers on 24-well plates were infected in triplicate wells with either wild-type strain 2457T, plasmidless strain M4243A, ΔaroA CVD 1201 (Noriega et al, (1994), supra) or AguaB-A CVD 1204, at a 50:1 ratio for 60 min. Then, the extracellular organisms were killed by addition of 100 µg/ml of gentamicin for 30 min, the plates were washed with sterile phosphate buffered saline (PBS)(0 hours time point), and thereafter incubated with 30 µg/ml of gentamicin for 4 more hours. The results are shown in Table 4 below.

Additional wells containing HeLa monolayers on coverslips were used to assess the percent of invasion at 0 and 4 hours under light microscopy after fixing with methanol and staining with Giemsa. The results are also shown in Table 4 below.

TABLE 4

Invasion and Intracellular Growth in HeLa Cells

| | | | | Intracellular cfu[a] (SD) | |
|---|---|---|---|---|---|
| Strain | Genotype | CR[b] | Invasion %[c] | 0 h | 4 h |
| 2457T | wild-type | + | 24 | $2.14 (0.4) \times 10^4$ | $6.83 (1.5) \times 10^5$ |
| M4243A | plasmidless | – | 0 | $6 (5.7) \times 10^1$ | 0 |
| CVD 1201 | ΔaroA | + | 28 | $2.3 (1) \times 10^4$ | $3.68 (0.7) \times 10^5$ |
| CVD 1204 | AguaB-A | + | 0.8 | $2.82 (1) \times 10^{2d}$ | $1.84 (0.3) \times 10^{3e}$ |

[a]Colony forming units
[b]Uptake of congo red dye
[c]Percent of invaded HeLa cells determined in over 400 HeLa cells observed
[d]CVD 1204 vs CVD 1201 at 0 h p = 0.007
[e]CVD 1204 vs CVD 1201 at 4 h p = 0.003

As shown in Table 4 above, in three different experiments, wild-type S. flexneri 2a strain 2457T efficiently invaded HeLa cells, and replicated in them over 30-fold in a 4 h period. Occasionally, a few cfu of the non-invasive plasmidless strain M4243A were detected, but none at 4 h, indicating that those organisms were probably extracellular.

ΔaroA CVD 1201 strain has been reported to be able to invade a HeLa tissue culture monolayer as efficiently as its

21 wild-type parent (Noriega et al, (1994), supra). However, as shown in Table 4 above, consistently fewer intracellular generations (i.e., 15-fold) were detected at 4 h.

Also as shown in Table 4 above, the mutant strain ΔguaB-A CVD 1204 was significantly less invasive for HeLa cells than its wild-type parent or the ΔaroA CVD 1201 strain counterpart (p=0.007), although its intracellular growth (i.e., 12-fold) was equivalent to that of the ΔaroA mutant.

EXAMPLE 3

Comparative Safety of Vaccine Candidate Strains CVD 1201, CVD 1204 and CVD 1205

In order to compare the attenuating effect of the ΔguaB-A deletion mutation in CVD 1204 and CVD 1205 with that of ΔaroA deletion mutation in CVD 1201, and to assess the safety of the double mutant ΔguaB-A, ΔvirG CVD 1205 strain, a randomized, comparative, keratoconjunctivitis safety test (Sereny test) was performed in guinea pigs using a blinded observer.

More specifically, bacterial cultures were grown overnight in trypticase soy agar (TSA) (BBL, Becton Dickinson, Cockeysville, Md.) containing 0.015% (w/v) Congo Red dye (SIGMA, St Louis, Mo.) (TSA-CR). Overnight cultures were harvested by adding 10 ml of PBS to each agar plate, and gently resuspending the bacteria with a sterile cotton tip applicator. The bacterial suspension was brought to an $OD_{600}$ of 0.5 (equivalent to $5.0 \times 10^8$ cfu/ml), and concentrated by centrifugation to the desired concentration ($10^{11}$ cfu/ml). Next, Hartley guinea pigs were inoculated in the conjunctival sac with $10^9$ cfu/10 µl PBS of wild-type strain 2457T or attenuated strains CVD 1201, CVD 1204, or CVD 1205. The guinea pigs were examined daily for 5 days, and their inflammatory response graded. The individual examining the guinea pigs each day and scoring the results was blinded as to what each animal had received and which eye had been inoculated. The statistical significance in the degree of the inflammatory response was calculated by a non-parametric sum of ranks (Mann-Whitney test). The overall frequency of occurrence of inflammation of any severity in the vaccine and control groups was compared by the Fisher's Exact test. The results are shown in Table 5 below.

22

An initial, mild, self-limited inflammatory response has been previously reported with ΔaroA S. flexneri 2a strains (Noriega et al, (1994) supra). As shown in Table 5 above, 24 h after a high-dose ($>10^9$ cfu/eye) inoculation, the frequency and severity of the initial inflammatory response was not significantly different between the ΔaroA strain CVD 1201 and the ΔguaB-A strain CVD 1204, although this mild inflammation resolved faster in the animals inoculated with CVD 1204. At 48 h, 6 out of 16 animals inoculated with CVD 1201, but none of the animals inoculated with CVD 1204, had residual signs of inflammation (p=0.018). Similarly, the double mutant ΔguaB-A, ΔvirG strain CVD 1205, induced a mild, self-limited, inflammatory response in fewer animals than the group challenged with the single mutant CVD 1204 (11 out of 16 vs. 5 out of 16) (p=0.04). At 72 h post-inoculation, the (blinded) observer grading the inflammatory response in the guinea pigs could not distinguish the inoculated eye from the non-inoculated one in any of the animals that received the attenuated mutants CVD 1201, CVD 1204 or CVD 1205, while all animals that received wild-type strain 2457T had a full-blown purulent keratoconjunctivitis.

EXAMPLE 4

Vaccination with ΔguaB-A, ΔvirG S. flexneri 2a Strain CVD 1205

A. Immune Response Against ΔguaB-A, ΔvirG S. flexneri 2a Strain CVD 1205

Overnight cultures of ΔguaB-A, ΔvirG S. flexneri 2a strain CVD 1205, grown on TSA-CR, and E. coli HS, a non-pathogenic, smooth, human commensal (Levine et al, Lancet, 1:1119–1122 (1978)), grown on TSA, were harvested and resuspended in PBS to an $OD_{600}$ of 0.5 (equivalent to $5.0 \times 10^8$ cfu/ml), and concentrated by centrifugation to the desired concentration of $10^{10}$ cfu/ml. Then, randomized, non-preconditioned Hartley guinea pigs were intranasally administered 100 µl of bacterial suspension (of either E. coli HS or CVD 1205) containing $10^9$ cfu. A booster dose was administered 14 days later in the identical manner. Then, 16 Hartley guinea pigs were randomly allocated to receive two intranasal immunizations, 2 weeks apart, of $10^{10}$ cfu of CVD 1205 or control strain E. coli HS. Tears were elicited by dried Capsicum baccatum flakes, and collected with 50 µl micropipettes (VWR Scientific,

TABLE 5

Sereny Test in Guinea Pigs of Vaccine-Candidate Strains CVD 1201, CVD 1204 and CVD 1205

| | | | Degree of Inflammation[a]/time | | | | | | | | | | | | | | |
|---|---|---|---|---|---|---|---|---|---|---|---|---|---|---|---|---|---|
| | | | 24 h | | | | | 48 h | | | | | 72 h | | | | |
| Strain | Genotype | No. | 0 | 1 | 2 | 3 | 4 | 0 | 1 | 2 | 3 | 4 | 0 | 1 | 2 | 3 | 4 |
| 2457T | wild-type | 8 | 0 | 0 | 2 | 2 | 4 | 0 | 0 | 0 | 0 | 8 | 0 | 0 | 0 | 0 | 8 |
| CVD 1201[b,c] | ΔaroA | 16 | 3 | 7 | 4 | 2 | 0 | 10 | 6 | 0 | 0 | 0 | 16 | 0 | 0 | 0 | 0 |
| CVD 1204[d] | ΔguaB-A | 16 | 5 | 10 | 1 | 0 | 0 | 16 | 0 | 0 | 0 | 0 | 16 | 0 | 0 | 0 | 0 |
| CVD 1205 | ΔguaB-A, ΔvirG | 16 | 11 | 1 | 3 | 1 | 0 | 15 | 1 | 0 | 0 | 0 | 16 | 0 | 0 | 0 | 0 |

[a] 0 = Normal
1 = Palpebral edema
2 = Palpebral edema with conjunctival hyperemia only
3 = Conjunctival hyperemia + slight exudate
4 = Full-blown purulent keratoconjunctivitis
[b] CVD 1201 vs. CVD 1204 at 24 h. Wilcoxon/Mann-Whitney p = 0.1. Fisher's Exact p = 0.68
[c] CVD 1201 vs. CVD 1204 at 48 h. Wilcoxon/Mann-Whitney p = 0.06. Fisher's Exact p = 0.02
[d] CVD 1204 vs. CVD 1205 at 24 h. Wilcoxon/Mann-Whitney p = 0.0.15. Fisher's Exact p = 0.04

Baltimore, Md.). Blood was obtained by anterior vena cava puncture (Whorton, Lab. Anim. Sci., 24:522–523 (1977)) under anesthesia with ketamine (Parke-Davis & Co., Morris Plains, N.J.) (44 mg/Kg i.p.) and acepromazine maleate (Ayerst Lab. Inc., NY, N.Y.) (1.2 mg/Kg i.p.). Samples were collected at days 0, 14 and 28 post-immunization. Mucosal and serum IgA and serum IgG antibodies against S. flexneri 2a LPS (phenol-water extraction (Baldwin et al, Infect. Immun., 58:761–765 (1990); and Westphal et al, Methods Carbohydr. Chem., 5:83–91 (1965)) from strain 2457T) were determined by ELISA using rabbit anti-guinea pig IgA-alpha chain (Bethyl Lab., Inc., Montgomery, Tex.), and a goat anti-guinea pig IgG (Kirkegaard and Perry Lab., Gaithersburg, Md.) antibodies, respectively. ELISA O.D. titers were log-transformed and compared by the Student's t-test. The results are shown in Table 7 below (mucosal IgA response), and Table 8 below (serum immune response).

TABLE 7

Mucosal IgA Immune Response Against S. flexneri 2a LPS Following Intranasal Immunization of Guinea Pigs with Strain CVD 1205 or Placebo

| Animal No. | Strain | Day 0 | Day 14 | Day 28 |
|---|---|---|---|---|
| 3 | CVD 1205[a] | 40 | 1280 | 10240 |
| 4 | CVD 1205[a] | 20 | 1280 | 20480 |
| 5 | CVD 1205[a] | 20 | 320 | 5120 |
| 7 | CVD 1205[a] | 20 | 1280 | 10240 |
| 8 | CVD 1205[a] | 20 | 5120 | 20480 |
| 11 | CVD 1205[a] | 20 | 1280 | 20480 |
| 14 | CVD 1205[a] | 20 | 640 | 10240 |
| 16 | CVD 1205[a] | 20 | 1280 | 20480 |
| GMT[g] | | 21.81 | 1173.76[c] | 13279.64[d] |
| 1 | HS[b] | 20 | 20 | 20 |
| 2 | HS[b] | 20 | 20 | 20 |
| 6 | HS[b] | 20 | 20 | 20 |
| 9 | HS[b] | 20 | 20 | 20 |
| 10 | HS[b] | 20 | 20 | 20 |
| 12 | HS[b] | 40 | 20 | 20 |
| 13 | HS[b] | 20 | 20 | 20 |
| 15 | HS[b] | 20 | 20 | 20 |
| GMT | | 21.81 | 20 | 20 |

[a]AguaA-B, ΔvirG S. flexneri 2a intranasal at days 0 and 14
[b]E. coli strain HS (control) intranasal at days 0 and 14
[c]CVD 1205 vs HS at 14 days, t test p = 0.0000008
[d]CVD 1205 vs HS at 28 days, t test p = 0.000000002
[e]3.0 × 10^7 cfu wild-type strain 2457T.
CVD 1205 vs HS (p = 0.0128).
[f]Not done. Animal No. 12 died as a consequence of anesthesia when bleeding at day 28.
[g]Geometric Mean Titers As shown in Table 7 above, a strong anti-S. flexneri 2a LPS mucosal IgA response was detected after a single dose of CVD 1205 (i.e., 54-fold rise in GMT). Furthermore, the second dose of CVD 1205, given at day 14, markedly boosted the IgA anti-LPS titers (11-fold over the primary response at day 14; 609-fold over day 0 or HS controls).

TABLE 8

Serum Immune Response Against S. flexneri 2a LPS After Immunization of Guinea Pigs with Vaccine Candidate Strain CVD 1205 or Placebo

| Animal No. | Strain | IgA | | IgG | |
|---|---|---|---|---|---|
| | | Day 0 | Day 28 | Day 0 | Day 28 |
| 3 | CVD 1205[a] | 12.5 | 800 | 12.5 | 1600 |
| 4 | CVD 1205[a] | 12.5 | 400 | 12.5 | 400 |
| 5 | CVD 1205[a] | 12.5 | 800 | 12.5 | 200 |
| 7 | CVD 1205[a] | 12.5 | 1600 | 12.5 | 800 |

TABLE 8-continued

Serum Immune Response Against S. flexneri 2a LPS After Immunization of Guinea Pigs with Vaccine Candidate Strain CVD 1205 or Placebo

| Animal No. | Strain | IgA | | IgG | |
|---|---|---|---|---|---|
| | | Day 0 | Day 28 | Day 0 | Day 28 |
| 8 | CVD 1205[a] | 12.5 | 1600 | 12.5 | 800 |
| 11 | CVD 1205[a] | 12.5 | 800 | 12.5 | 1600 |
| 14 | CVD 1205[a] | 12.5 | 1600 | 12.5 | 800 |
| 16 | CVD 1205[a] | 12.5 | 400 | 12.5 | 800 |
| GMT | | 12.5 | 975.21[c] | 12.5 | 724.58[d] |
| 1 | HS[b] | 12.5 | 12.5 | 12.5 | 12.5 |
| 2 | HS[b] | 12.5 | 12.5 | 12.5 | 12.5 |
| 6 | HS[b] | 12.5 | 12.5 | 12.5 | 12.5 |
| 9 | HS[b] | 12.5 | 12.5 | 12.5 | 12.5 |
| 10 | HS[b] | 12.5 | 12.5 | 12.5 | 12.5 |
| 12 | HS[b] | 12.5 | 12.5 | 12.5 | 12.5 |
| 13 | HS[b] | 12.5 | 12.5 | 12.5 | 12.5 |
| 13 | HS[b] | 12.5 | 12.5 | 12.5 | 12.5 |
| GMT | | 12.5 | 12.5 | 12.5 | 12.5 |

[a]AguaB-A, ΔvirG S. flexneri 2a intranasal at days 0 and 14
[b]E. Coli strain HS (control) intranasal at days 0 and 14
[c]CVD 1205 vs HS t test p = 0.0000003
[d]CVD 1205 vs HS t test p = 0.000003

As shown in Table 8 above, the serum antibody response was more delayed, as no serum IgG or IgA anti-Shigella LPS was detected after the first immunization. However, after the second immunization, those animals immunized with CVD 1205 had specific anti-S. flexneri 2a LPS IgA (i.e., 78-fold in GMT) and IgG (i.e., 60-fold in GMT) titers that were highly significant with respect to those obtained at day 0 in the same guinea pigs or at day 0 and 28 in the HS controls.

B. Protection of Guinea Pigs Against Wild-Type Challenge

On the 28th day after the first immunization, the 16 guinea pigs that had received CVD 1205 or placebo were challenged with $3.0 \times 10^7$ cfu of wild-type S. flexneri 2a strain 2457T in 10 µl of PBS. Full-blown purulent keratoconjunctivitis developed in 5 of 7 control animals vaccinated with placebo (71% attack rate) versus none of the 8 guinea pigs immunized with two spaced intranasal doses of CVD 1205 (vaccine efficacy=100%, p=0.0069).

EXAMPLE 5

Expression of Foreign Genes in shigella: Integration of LTA₂B of ETEC in the ΔguaB-A Allele of Shigella Vaccine Strain CVD 1205

Genomic DNA of wild-type ETEC strain H10407 (O78:H11; heat-labile (LT) and heat-stable enterotoxin positive), which has caused diarrhea in volunteer studies at the CVD (Tacket et al, N. Eng. J. Med., 318:1240–1243, (1988)), was used as the template for the construction of a LTA₂B allele. Strain H10407 is available from the CVD strain collection.

More specifically, a 5' terminus DNA segment of LT that includes the entire natural promoter and the A₁ subunit signal sequence was PCR-amplified using the following primers:

5'-CGCGGATCCGCGATCCCTCGCATGGATGTTTT
ATAAAAAACAT-3' (SEQ ID NO:12), and

5'-TGTTCTTCGCGATGGCGATGCTAATAAAATAA
AAAAAATGAA-3'

(SEQ ID NO:13), and then fused to a 3' DNA segment that included the whole A₂ and B subunits, and that was amplified using the following primers:

5'-TCGCCATCGCGAAGAACAATTACAGGTGATAC
TTGTAATGAG-3' (SEQ ID NO:14), and

5'-GGGGGGCCCGGTCTAGTTTTCCATACTGATTG
CCGCAATTGA-3' (SEQ ID NO:15).

The extreme primers (SEQ ID NOS:12 and 15) include BamHI and ApaI restriction sites (underlined) for cloning into the BamHI-ApaI sites in the middle of the ΔguaB-A allele in pFM729. The internal primers (SEQ ID NOS:13 and 14) include a homologous region (in bold) used in the fusion of the 5' and 3' segments was introduced. The region included a unique restriction site (NruI). This NruI site could be used in the future for the introduction of small foreign genes which would express proteins fused to the signal sequence of the $A_1$ subunit in their N-terminus and the entire $A_2$ subunit in the C-terminus.

The resulting ΔLTA$_2$B allele has an in-frame deletion mutation corresponding to 90% of the enzymatically active $A_1$ subunit, in which the signal sequence of the $A_1$ subunit (SS) was fused in-frame with the entire $A_2$ subunit using the same PCR methods described in the construction of the ΔguaB-A allele. As a result, the molecule is exported to the periplasmic space. The $A_2$ subunit was conserved to give stability to the B subunit pentamer formation.

This LTA$_2$B allele was cloned in the unique restriction sites BamHI and ApaI that were introduced in the middle of the ΔguaB-A allele in pFM726A (suicide plasmid), giving rise to pAH101.

Figure 6:
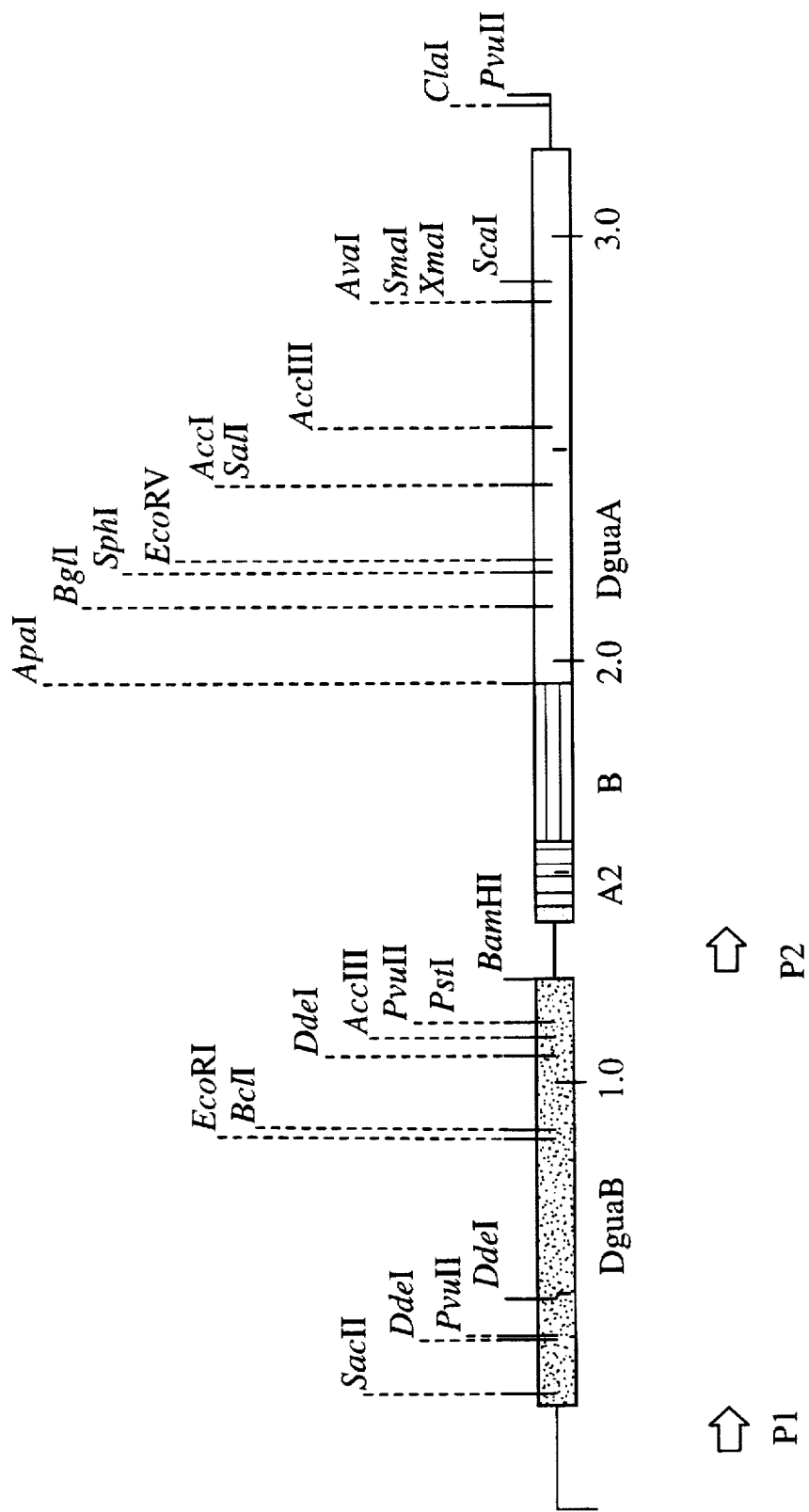
FIG. 6 is a schematic representation of the integration of LTA₂B in the ΔguaB-A allele.

The chromosomal integration of LTA$_2$B, into the ΔguaB-A allele of ΔguaB-A, ΔvirG S. flexneri 2a strain CVD 1205 was performed by homologous recombination of the ΔguaB-A allele in CVD 1205 by the ΔguaB-A::LTA$_2$B allele in pAH101, as described by Blomfield et al, supra; and Noriega et al, (1994) supra. The resulting strain was designated as CVD 1205 Ω(ΔguaB-A::LTA$_2$B). A schematic representation of the integration of LTA$_2$B in the ΔguaB-A allele is shown in FIG. 6.

To asses the expression, periplasmic exportation and receptor binding capability of recombinant LTA$_2$B expressed in Shigella, 5.0 ml cultures of CVD 1205 Ω(ΔguaB-A::LTA$_2$B)and controls were treated with 600 μg of polymyxin B (to release LTA$_2$B from the periplasmic space) as described by Evans Jr. et al, Infect. Immun., 10:1010–1017 (1974). Then, a GM$_1$ ganglioside-capture ELISA was performed, as described by Sanchez et al, J. Clin. Microbiol., 28:2175–2177 (1990). The amount of toxin produced by the recombinant constructs was calculated in reference to purified LT. The results are shown in Table 9 below.

TABLE 9

Chromosomally Integrated LTA$_2$B
Expressed by CVD 1205

| Strain | μg of LTA$_2$B/ml of polymyxin B-treated culture |
|---|---|
| CVD 1205 | 0 |
| CVD 1205 Ω(ΔguaB-A::LTA$_2$B) | 2.32 |
| H10407 | 0.23 |

As shown in Table 9 above, high levels of expression can be achieved with chromosomally encoded LTA$_2$B in the attenuated Shigella vaccine candidate CVD 1205. The immunogenicity of LTA$_2$B expressed in Shigella has not yet been tested. However, in parallel investigations, ΔaroC, ΔaroD S. typhi strain CVD 908 (Hone et al, supra), and ΔaroC, ΔaroD S. paratyphi B strain CVD 950 were transformed with pAH102 (a medium copy number plasmid encoding the LTA$_2$B gene). These constructs elicited very high serum anti-LT IgG antibody titers in mice after intranasal immunization (up to >1:100,000 vs. <1:25 in un-immunized controls), thereby demonstrating the immunogenicity of the recombinant LTA$_2$B molecule.

EXAMPLE 6

ΔguaB-A, ΔvirG, ΔstxA S. dysenteriae Type 1
Vaccine Strain CVD 1252

A. Construction of CVD 1252

Wild-type parent S. dysenteriae type 1 strain 1617 (also known as A-1) is known to be virulent based on experimental challenge studies in adult volunteers (Levine et al, (1973) supra). Strain 1617 was isolated from a child with dysentery in Guatemala prior to the 1960's Central American Shiga dysentery pandemic. This strain is one of the very few, fully virulent S. dysenteriae type 1 strains in the world that does not carry a R (antibiotic resistance) factor.

The same strategy described for the construction of CVD 1205 was employed to introduce ΔguaB-A and ΔvirG mutations in S. dysenteriae type 1 strain 1617. That is, homologous recombination was preformed with the ΔguaB-A allele in pFM726A with strain 1617 in the same manner as described in the construction of strain CVD 1205. The deletion mutation in the guaB-A allele of strain 1617 was confirmed by negative radio-labeled probing with:

5'-GGGCGGCCTGCGCTCCTGTATGGGTCTGACCG
GCTGTGGT-3' (SEQ ID NO: 6); and PCR using the following primers 5'-CGAGCTCGCGAGCTCGGTAAAGTACCAGTGA
CCGGAAGCTGGTTGCGT-3' (SEQ ID NO:2); and 5'-GCTCTAGAGCTCTAGAGCTCATTCCCACTCAA
TGGTAGCTGGCGGCTT-3' (SEQ ID NO:5), as described for the construction and screening of ΔguaB-A S. flexneri 2a strain CVD 1204, giving rise to strain ΔguaB-A S. dysenteriae 1. As in the case with strain CVD 1204, this strain is not able to grow in minimal medium unless supplemented with 10 mg/l of guanine.

Next, Shiga toxin, the potent entero/cyto/neurotoxin produced by this serotype, was inactivated. More specifically, strain ΔguaB-A S. dysenteriae 1 was electroporated with pJW101, a temperature-sensitive deletion cassette based on the pSC101 replicon, that contains a Δstx allele with a 495 bp deletion mutation in the stxA gene that effectively inactivated the cytotoxicity of Shiga toxin in HeLa cells.

pJW101 was constructed by amplifying the Δstx allele from a plasmid containing stxA-B (pNAS13) (Strockbine et al, J. Bacteriology, 170:1116–1122 (1988) ) in which a 495 bp segment was deleted by cutting with HpaI and NruI, and re-circularizing with T4 ligase (obtained from Clare K. Schmitt and Alison D. O'Brien, USUHS, Bethesda, Md.). The Δstx allele thus generated was amplified with the following primers:

5'-GGGGGGATCCATGAAAATAATTATTTTTAGAG
TGCT-3' (SEQ ID NO:16), and

5'-GGGGTCGACTCAACGAAAAATAACTTCGCTG
AATCC-3' (SEQ ID NO:17), in which the restriction sites BamHI and SalI (underlined) were added for cloning. This Δstx allele was cloned in the unique restriction sites BamHI and SalI of pIB307, to which a sacB-neo$^r$ cassette was subcloned from pIB279, as described by Heustersprente et al, Gene, 53:299–300 (1987); and Noriega et al, (1994) supra, giving rise to ΔguaB-A, ΔstxA S. dysenteriae 1.

After homologous recombination in strain ΔguaB-A S. dysenteriae 1, the ΔstxA deletion mutation was confirmed phenotypically by a HeLa cell cytotoxicity assay, as described by O'Brien et al, *J. Infect. Dis.*, 146:763–769 (1982), and genotypically by lack of hybridization with a radio-labeled oligonucleotide probe:

5'-GTCGCATAGTGGAACCTCACTGACGCAGTCTGTGGCAAGAGCG-3'

(SEQ ID NO:18), which contains the sequence within the deleted portion of Shiga toxin subunit A gene; and by PCR-amplification with the primers described above, which yielded a 700 bp PCR-product, compared to a 1.3 Kbp PCR-product obtained by amplifying the wild-type stx operon.

A third deletion mutation in the virulence gene virG was introduced into ΔguaB-A, ΔstxA *S. dysenteriae* 1 as described by Noriega et al. (1994) supra. The resulting ΔguaB-A, ΔstxA, ΔvirG *S. dysenteriae* type 1 was named strain CVD 1252, and has been deposited at the American Type Culture Collection on Apr. 9, 1996, under ATCC No. 55759.

B. Safety of ΔguaB-A, ΔvirG, ΔstxA *S. dysenteriae* Type 1 Strain CVD 1252 in the Guinea Pig Keratoconjunctivitis Test (Sereny test)

Ten guinea pigs were randomized and inoculated in the conjunctival sac with 10 µl of a suspension containing $10^9$ cfu of the wild-type parent or the vaccine strain CVD 1252. The guinea pigs were examined daily for 4 days, and their inflammatory response to the inoculated organism graded. Statistical significance in the proportion of animals in each group exhibiting any inflammatory response (i.e., animals with scores of 0 versus those with scores of 1–4) was calculated by Fisher's Exact test. The results are shown in Table 10 below.

TABLE 11

Mucosal IgA Immune Response Against *S. dysenteriae* 1 LPS following Intranasal Immunization of Guinea Pigs with Strain CVD 1252 or Placebo

| Animal No. | Strain | Day 0 | Day 14 | Day 28 |
|---|---|---|---|---|
| 7 | CVD 1252[a] | 20 | 40 | 2560 |
| 18 | CVD 1252[a] | 20 | 40 | 640 |
| 21 | CVD 1252[a] | 20 | 40 | 20480 |
| 28 | CVD 1252[a] | 20 | 320 | 20480 |
| 38 | CVD 1252[a] | 20 | 20 | 640 |
| 40 | CVD 1252[a] | 20 | 80 | 1280 |
| 43 | CVD 1252[a] | 20 | 40 | 320 |
| 46 | CVD 1252[a] | 20 | 80 | 620 |
| 47 | CVD 1252[a] | 20 | 1280 | 10240 |
| 49 | CVD 1252[a] | 20 | 20 | 1280 |
| GMT | | | | 2072.8[c] |
| 8 | HS[b] | 20 | 20 | 20 |
| 10 | HS[b] | 20 | 20 | 20 |
| 15 | HS[b] | 20 | 20 | 20 |
| 17 | HS[b] | 20 | 20 | 20 |
| 19 | HS[b] | 20 | 20 | 20 |
| 25 | HS[b] | 40 | 20 | 20 |
| 27 | HS[b] | 20 | 20 | 20 |
| 32 | HS[b] | 20 | 20 | 20 |
| 36 | HS[b] | 20 | 40 | 40 |
| 50 | HS[b] | 20 | 20 | 20 |
| GMT | | | | 21.4 |

[a]ΔguaB-A, ΔvirG ΔstxA *S. dysenteriae* 1 strain intranasal at days 0 and 14
[b]*E. coli* strain HS (control) intranasal at days 0 and 14
[c]CVD 1252 vs HS at 28 days, t test p = 0.000002

As shown in Table 11 above, strain CVD 1252 elicited a strong anti-S. dysenterie 1 LPS SIgA response.

TABLE 10

Safety (Sereny) Test in Guinea Pigs of Vaccine-Candidate Strain CVD 1252

| | | | Degree of Inflammation[a]/time | | | | | | | | | | | | | |
|---|---|---|---|---|---|---|---|---|---|---|---|---|---|---|---|---|
| | | | 24 h | | | | | 48 h | | | | | 72 h | | | | |
| Strain | Genotype | No. | 0 | 1 | 2 | 3 | 4 | 0 | 1 | 2 | 3 | 4 | 0 | 1 | 2 | 3 | 4 |
| 1617 | wild-type | 5 | 0 | 2 | 3 | 0 | 0 | 0 | 0 | 0 | 1 | 4 | 0 | 0 | 0 | 0 | 5 |
| CVD 1252[b] | guaB-A, stxA, virG | 5 | 5 | 0 | 0 | 0 | 0 | 5 | 0 | 0 | 0 | 0 | 5 | 0 | 0 | 0 | 0 |

[a]0 = Normal
1 = Palpebral edema
2 = Palpebral edema with conjunctival hyperemia only
3 = Conjunctival hyperemia + slight exudate
4 = Full-blown purulent keratoconjunctivitis
[c]CVD 1252 vs. 1617 at 24, 48 and 72 h, Fisher's Exact p = 0.008

As shown in Table 10 above, no inflammatory response was observed in the guinea pigs that received CVD 1252.

C. Mucosal immune response elicited by ΔguaB-A, ΔvirG, ΔstxA *S. dysenteriae* Type 1 Strain CVD 1252

Hartley guinea pigs were immunized intranasally with $10^9$ cfu of strain CVD 1252, and their tears collected and analyzed as described above for strain CVD 1205. The results are shown in Table 11 below.

D. Protection Against Keratoconjunctivitis in Guinea Pigs Immunized Intranasally with CVD 1252 or Placebo In order to test the protective immunogenicity of *S. dysenteriae* 1 CVD 1252, 10 Hartley guinea pigs were randomly allocated to receive two intranasal immunizations, 2 weeks apart, of $10^{10}$ cfu of CVD 1252 or control strain *E. coli* HS. On the 28th day after the first immunization, the 10 guinea pigs that had received CVD 1205 or placebo were challenged with $9.0 \times 10^7$ cfu of wild-type *S. dysenteriae* 1 strain 1617 in 10 µl of PBS. Full-blown purulent keratoconjunctivitis developed in 5 of 9 control animals vaccinated with placebo (one animal died during sample collection) (55% attack rate) versus none of the 10 guinea pigs immunized with two spaced nasal doses of CVD 1252 (vaccine efficacy=100%, p=0.05).

EXAMPLE 7

Construction of ΔguaB-A, ΔvirG *S. sonnei* vaccine strain CVD 1231

Wild-type parent *S. sonnei* strain 53G, which is known to be virulent based on experimental challenge studies in adult volunteers at the CVD (Herrington et al. supra), was attenuated in the same manner as described for CVD 1205, i.e., with specific deletion mutations in the guaB, guaA and virG alleles. The resulting mutant, ΔguaB-A, ΔvirG *S. sonnei*, was designated CVD 1231. CVD 1231 has been deposited at the American Type Culture Collection on Apr. 9, 1996, under ATCC No. 55758.

While the invention has been described in detail, and with reference to specific embodiments thereof, it will be apparent to one of ordinary skill in the art that various changes and modifications can be made therein without departing from the spirit and scope thereof.

What is claimed is:

1. A Shigella mutant which is incapable of forming de novo guanine nucleotides, wherein said mutant contains a deletion mutation in the guaB-A operon.

2. The Shigella mutant of claim 1, wherein said mutation is a deletion mutation, and said deletion mutation is in the guaA gene, the guaB gene, or in both the guaA gene and the guaB gene.

3. The Shigella mutant of claim 1, wherein said mutant encodes and expresses a foreign antigen.

4. The Shigella mutant of claim 2, wherein said deletion mutation is in both the guaA gene and the guaB gene.

5. The Shigella mutant of claim 1, wherein said Shigella is a serotype selected from the group consisting of *Shigella flexneri, Shigella dysenteriae, Shigella boydii* and *Shigella sonnei*.

6. The Shigella mutant of claim 5, wherein said Shigella is a *Shigella flexneri* species selected from the group consisting of *S. flexneri* 2a, *S. flexneri* 3a and *S. flexneri* 6.

7. The Shigella mutant of claim 5, wherein said Shigella is a *Shigella dysenteriae* selected from the group consisting of strain 7/87 and strain 1617.

8. The Shigella mutant of claim 5, wherein said Shigella is a *Shigella sonnei* selected from the group consisting of strain G53 and strain 482-79.

9. The Shigella mutant of claim 4, wherein said mutant has an $aro^-$ and virG phenotype.

10. The Shigella mutant of claim 9, wherein said mutant has an a deletion in the set1 gene, the sen gene or both the set1 gene and the sen gene.

11. The Shigella mutant of claim 4, wherein said mutation is introduced into parent strain *Shigella flexneri* 2a strain CVD1203 (ATCC No. 55556).

12. The Shigella mutant of claim 4, wherein said mutant is ΔguaB-A, ΔvirG *Shigella flexneri* 2a strain CVD1205 (ATCC No. 55757).

13. The Shigella mutant of claim 4, wherein said mutant is ΔguaB-A, ΔstxA, ΔvirG *Shigella dysenteriae* type 1 strain CVD 1252 (ATCC No. 55759).

14. The Shigella mutant of claim 4, wherein said mutant is the ΔguaB-A, ΔvirG *Shigella sonnei* CVD 1231 (ATCC No. 55758).

15. The Shigella mutant of claim 1, wherein said mutant contains a plasmid which encodes and expresses, in a eukaryotic cell, a foreign gene.

16. A vaccine against Shigellosis comprising:

(A) a pharmaceutically effective amount of a Shigella mutant which is incapable of forming de novo guanine nucleotides, wherein said mutant contains a deletion mutation in the guaB-A operon; and (B) a pharmaceutically acceptable carrier or diluent.

17. The vaccine of claim 16, wherein said pharmaceutically effective amount is about $10^5$ cfu to $10^{10}$ cfu.

18. The vaccine of claim 16, wherein said mutant encodes and expresses a foreign antigen.

19. The vaccine of claim 18, wherein said pharmaceutically effective amount is about $10^5$ cfu to $10^{10}$ cfu.

20. The vaccine of claim 16, wherein said mutant contains a plasmid which encodes and expresses, in a eukaryotic cell, a foreign gene.

21. The vaccine of claim 20, wherein said pharmaceutically effective amount is about $10^5$ cfu to $10^{10}$ cfu.

* * * * *

UNITED STATES PATENT AND TRADEMARK OFFICE
CERTIFICATE OF CORRECTION

| | | |
|---|---|---|
| PATENT NO. | : 5,783,196 | Page 1 of 1 |
| APPLICATION NO. | : 08/629600 | |
| DATED | : July 21, 1998 | |
| INVENTOR(S) | : Myron M. Levine and Fernando Noriega | |

It is certified that error appears in the above-identified patent and that said Letters Patent is hereby corrected as shown below:

Insert at Column 1, line 10 the heading --STATEMENT REGARDING FEDERALLY SPONSORED RESEARCH OR DEVELOPMENT--

Insert at Column 1, following the above heading --This invention was made with government support under NIH Grant No. AI029471 awarded by the National Institutes of Health. The government has certain rights in the invention.--

Signed and Sealed this

Eighteenth Day of March, 2008

JON W. DUDAS
*Director of the United States Patent and Trademark Office*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 3531 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( x i ) SEQUENCE DESCRIPTION: SEQ ID NO:1:

```
GTAAAGTACC AGTGACCGGA AGCTGGTTGC GTGAAATTAG AAATTTCGCC GCTGATCCAA      60
ACCTGTCCCA TCTCATGCTC AAGCAGCAGA CGAACCGTTT GATTCAGGCG ACTAACGGTA     120
AAAATTGCAG GGGATTGAGA AGGTAACATG TGAGCGAGAT CAAATTCTAA ATCAGCAGGT     180
TATTCAGTCG ATAGTAACCC GCCCTTCGGG GATAGCAAGC ATTTTTTGCA AAAAGGGGTA     240
GATGCAATCG GTTACGCTCT GTATAATGCC GCGGCAATAT TTATTAACCA CTCTGGTCGA     300
GATATTGCCC ATGCTACGTA TCGCTAAAGA AGCTCTGACG TTTGACGACG TTCTCCTCGT     360
TCCTGCTCAC TCTACCGTTC TGCCGAATAC TGCTGACCTC AGCACCCAGC TGACGAAAAC     420
TATTCGTCTG AATATCCCTA TGCTTTCCGC AGCAATGGAT ACCGTAACGG AAGCGCGCCT     480
GGCTATTGCT CTGGCTCAGG AAGGCGGTAT CGGCTTTATC CACAAAAACA TGTCCATTGA     540
ACGCCAGGCA GAAGAAGTTC GCCGTGTGAA AAAACACGAA TCTGGTGTGG TGACTGATCC     600
GCAGACTGTT CTGCCAACCA CGACGCTGCG CGAAGTGAAA GAACTGACCG AGCGTAACGG     660
TTTTGCGGGC TATCCGGTCG TTACCGAAGA AAACGAACTG GTGGGTATTA TCACCGGTCG     720
TGACGTGCGT TTTGTTACCG ACCTGAACCA GCCGGTTAGC GTTTACATGA CGCCGAAAGA     780
GCGTCTGGTC ACCGTGCGTG AAGGTGAAGC CCGTGAAGTG GTGCTGGCAA AAATGCACGA     840
AAAACGCGTT GAAAAAGCGC TGGTGGTTGA TGACGAATTC CACCTGATCG GCATGATCAC     900
CGTGAAAGAC TTCCAGAAAG CGGAAGCTAA ACCGAACGCC TGTAAAGACG AGCAAGGCCG     960
TCTGCGTGTT GGTGCAGCGG TTGGCGCAGG TGCGGGTAAC GAAGAGCGTG TTGACGCGCT    1020
GGTTGCCGCA GGCGTTGACG TTCTGCTGAT CGACTCCTCC CACGGTCACT CAGAAGGTGT    1080
ACTGCAACGT ATCCGTGAAA CCCGTGCTAA ATATCCGGAT CTGCAAATTA TCGGCGGCAA    1140
CGTGGCAACA GCTGCAGGTG CACGCGCTCT GGCAGAAGCT GGTTGCAGTG CGGTTAAAGT    1200
CGGCATTGGC CCTGGCTCTA TCTGTACAAC TCGTATCGTG ACTGGCGTCG GTGTTCCGCA    1260
GATTACCGCT GTTGCTGACG CAGTAGAAGC CCTGGAAGGC ACCGGTATTC CGGTTATCGC    1320
```

-continued

```
TGATGGCGGT ATTCGCTTCT CCGGCGACAT CGCCAAAGCT ATCGCCGCTG GCGCAAGCGC   1380
GGTGATGGTA GGTTCCATGC TGGCGGGTAC TGAAGAATCT CCGGGTGAAA TCGAACTCTA   1440
CCAGGGCCGT TCTTACAAAT CTTACCGTGG TATGGGTTCC CTGGGCGCGA TGTCCAAAGG   1500
TTCCTCTGAC CGTTATTTCC AGAGCGATAA CGCTGCCGAC AAACTGGTGC CGGAAGGTAT   1560
CGAAGGTCGC GTAGCCTATA AAGGTCGCCT GAAAGAGATC ATTCACCAGC AGATGGGCGG   1620
CCTGCGCTCC TGTATGGGTC TGACCGGCTG TGGTACTATC GACGAACTGC GTACTAAAGC   1680
GGAGTTTGTA CGTATCAGCG GTGCGGGCAT TCAGGAAAGC CACGTTCACG ACGTGACCAT   1740
TACTAAAGAG TCCCCGAACT ACCGTCTGGG CTCCTGATTC TCTTCGCCCG ACTTCATGTC   1800
GGGCGATTTA TATTATCTGT TTCACTTGCC TCGGAATAAG CGTCAATGAC GGAAAACATT   1860
CATAAGCATC GCATCCTCAT TCTGGACTTC GGTTCTCAGT ACACTCAACT GGTTGCGCGC   1920
CGCGTGCGTG AGCTGGGTGT TTACTGCGAA CTGTGGGCGT GGGATGTGAC AGAAGCACAA   1980
ATTCGTGACT TCAATCCAAG CGGCATTATT CTTTCGGCG GCCCGGAAAG TACTACTGAA    2040
GAAAACAGTC CGCGTGCGCC GCAGTATGTC TTTGAAGCAG CGTACCGGT ATTCGGCGTT    2100
TGCTATGGCA TGCAGACCAT GGCAATGCAG TTGGGCGGTC ACGTTGAAGC CTCTAACGAA   2160
CGTGAATTTG GCTACGCGCA GGTTGAAGTC GTAAACGACA GCGCACTGGT TCGCGGTATC   2220
GAAGATGCGC TGACCGCAGA CGGTAAACCG CTGCTCGATG TCTGGATGAG CCACGGCGAT   2280
AAAGTTACCG CTATTCCGTC CGACTTCATC ACCGTAGCCA GCACCGAAAG CTGCCCGTTT   2340
GCCATTATGG CTAACGAAGA AAAACGCTTC TATGGCGTAC AGTTCCACCC GGAAGTGACT   2400
CATACCCGCC AGGGTATGCG CATGCTGGAG CGTTTTGTGC GTGATATCTG CCAGTGTGAA   2460
GCCCTGTGGA CGCCAGCGAA AATTATCGAC GATGCTGTAG CTCGCATCCG CGAGCAGGTA   2520
GGCGACGATA AAGTCATCCT CGGCCTCTCT GGTGGTGTGG ATTCCTCCGT AACCGCAATG   2580
CTGCTGCACC GCGCTATCGG TAAAAACCTG ACTTGCGTAT TCGTCGACAA CGGCCTGCTG   2640
CGCCTCAACG AAGCAGAGCA GGTTCTGGAT ATGTTTGGCG ATCACTTTGG TCTTAACATT   2700
GTTCACGTAC CGGCAGAAGA TCGCTTCCTG TCAGCGCTGG CTGGCGAAAA CGATCCGGAA   2760
GCAAAACGTA AAATCATCGG TCGCGTTTTC GTTGAAGTAT TCGATGAAGA AGCGCTGAAA   2820
CTGGAAGACG TGAAGTGGCT GGCGCAGGGC ACCATCTACC CTGACGTTAT CGAATCTGCG   2880
GCGTCTGCAA CCGGTAAAGC ACACGTCATC AAATCTCACC ACAACGTGGG CGGCCTGCCG   2940
AAAGAGATGA AGATGGGCCT GGTTGAACCG CTGAAAGAGC TGTTCAAAGA CGAAGTGCGT   3000
AAGATTGGTC TGGAGCTGGG CCTGCCGTAC GACATGCTGT ACCGTCACCC GTTCCCGGGA   3060
CCAGGCCTTG GCGTTCGTGT TCTGGGTGAA GTGAAGAAAG AGTACTGTGA CCTGCTGCGC   3120
CGTGCTGACG CCATCTTCAT TGAAGAACTG CGTAAGCGG ACCTGTACGA CAAAGTCAGC    3180
CAGGCGTTCA CTGTGTTCCT GCCGGTACGT TCCGTTGGCG TAATGGGCGA TGGTCGTAAG   3240
TATGACTGGG TTGTCTCTCT GCGTGCTGTC GAAACCATCG ACTTTATGAC CGCACACTGG   3300
GCGCATCTGC CGTACGATTT CCTCGGTCGC GTTTCCAACC GCATTATCAA TGAAGTGAAC   3360
GGTATTTCCC GCGTGGTGTA TGACATCAGC GGCAAGCCGC CAGCTACCAT TGAGTGGGAA   3420
TGATTTGACC CTGCACTATG AATGAACAAA ACCCTCTGTT ACTACAGAGG GTTTTTTATC   3480
TTCAAGAATT ATAGGATTGA AGTTACTAAC ATCGATTAAT TAAACCAGCT G            3531
```

( 2 ) INFORMATION FOR SEQ ID NO:2:

( i ) SEQUENCE CHARACTERISTICS:
( A ) LENGTH: 48 base pairs
( B ) TYPE: nucleic acid (C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:2:

CGAGCTCGCG AGCTCGGTAA AGTACCAGTG ACCGGAAGCT GGTTGCGT  48

(2) INFORMATION FOR SEQ ID NO:3:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:3:

GGGCCCGGGG GATCCTCAAC CGACGCCAGT CACGATACGA GTTGTACAGA T  51

(2) INFORMATION FOR SEQ ID NO:4:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:4:

TGAGGATCCC CCGGGCCCGG CTACGCGCAG GTTGAAGTCG TAAACGACAG C  51

(2) INFORMATION FOR SEQ ID NO:5:

(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:5:

GCTCTAGAGC TCTAGAGCTC ATTCCCACTC AATGGTAGCT GGCGGCTT  48

(2) INFORMATION FOR SEQ ID NO:6:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:6:

GGGCGGCCTG CGCTCCTGTA TGGGTCTGAC CGGCTGTGGT  40

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:7:

GGGGAATTCC AAATTCACAA ATTTTTTTGT    30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:8:

TCCATGCCAT TCATGGAGTA TTAATGAATT    30

( 2 ) INFORMATION FOR SEQ ID NO:9:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:9:

CTCCATGAAT GGCATGGAAA GGCGGAATA    29

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:10:

CGGGTCGACT CAGAAGGTAT ATTTCACACC CAA    33

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:11:

GGGGACAGTT GAAGCTATGA CACGTACCGC TGGTGTTATT          40

( 2 ) INFORMATION FOR SEQ ID NO:12:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:12:

CGCGGATCCG CGATCCCTCG CATGGATGTT TTATAAAAA CAT          43

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:13:

TGTTCTTCGC GATGGCGATG CTAATAAAAT AAAAAAATG AA          42

( 2 ) INFORMATION FOR SEQ ID NO:14:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:14:

TCGCCATCGC GAAGAACAAT TACAGGTGAT ACTTGTAATG AG          42

( 2 ) INFORMATION FOR SEQ ID NO:15:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:15:

GGGGGGCCCG GTCTAGTTTT CCATACTGAT TGCCGCAATT GA          42

( 2 ) INFORMATION FOR SEQ ID NO:16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (i i) MOLECULE TYPE: DNA (i i i) HYPOTHETICAL: NO (x i) SEQUENCE DESCRIPTION: SEQ ID NO:16:

GGGGGGATCC ATGAAAATAA TTATTTTAG AGTGCT        36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (x i) SEQUENCE DESCRIPTION: SEQ ID NO:17:

GGGGTCGACT CAACGAAAAA TAACTTCGCT GAATCC        36

(2) INFORMATION FOR SEQ ID NO:18:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (x i) SEQUENCE DESCRIPTION: SEQ ID NO:18:

GTCGCATAGT GGAACCTCAC TGACGCAGTC TGTGGCAAGA GCG        43